United States Patent
Anderson et al.

(10) Patent No.: US 10,752,648 B2
(45) Date of Patent: Aug. 25, 2020

(54) MAGNETIC IONIC LIQUIDS, METHODS OF MAKING AND USES THEREOF AS SOLVENTS IN THE EXTRACTION AND PRESERVATION OF NUCLEIC ACIDS

(71) Applicant: The University of Toledo, Toledo, OH (US)

(72) Inventors: Jared L. Anderson, Ames, IA (US); Omprakash Nacham, Toledo, OH (US); Kevin D. Clark, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/295,581

(22) Filed: Mar. 7, 2019

(65) Prior Publication Data

US 2019/0194643 A1    Jun. 27, 2019

Related U.S. Application Data

(62) Division of application No. 15/048,265, filed on Feb. 19, 2016, now Pat. No. 10,280,416.

(60) Provisional application No. 62/118,901, filed on Feb. 20, 2015.

(51) Int. Cl.
| | | |
|---|---|---|
| *C07F 15/02* | (2006.01) | |
| *C12N 15/10* | (2006.01) | |
| *C12P 19/34* | (2006.01) | |

(52) U.S. Cl.
CPC .......... *C07F 15/025* (2013.01); *C12N 15/101* (2013.01); *C12N 15/1013* (2013.01); *C12P 19/34* (2013.01)

(58) Field of Classification Search
CPC .................................................... C07F 15/025
See application file for complete search history.

(56) References Cited

PUBLICATIONS

Nacham et al. "Synthetic Strategies for Tailoring the Physicochemical and Magnetic Properties of Hydrophobic Magnetic Ionic Liquids" Chem. Mater. 2015, vol. 27, No. 3, pp. 923-931.*

Likhanova et al. "Ionic liquids screening for desulfurization of natural gasoline by liquid-liquid extraction" Mol. Divers. 2010, vol. 14, No. 4, pp. 777-787.*

* cited by examiner

*Primary Examiner* — Joseph R Kosack
(74) *Attorney, Agent, or Firm* — MacMillan, Sobanski & Todd, LLC

(57) ABSTRACT

Described herein are methods for making and using magnetic ionic liquid that have at least one cationic component and at least one anionic component, where at least one of the cationic components or the anionic components is a paramagnetic component. The magnetic ionic liquids are capable of manipulation by an external magnetic field.

1 Claim, 19 Drawing Sheets
(10 of 19 Drawing Sheet(s) Filed in Color)
Specification includes a Sequence Listing.

Monocationic Hydrophobic Magnetic Ionic Liquids

Dicationic Hydrophobic Magnetic Ionic Liquids

Tricationic Hydrophobic Magnetic Ionic Liquids

Scheme 1. Synthesis of Monocationic and Dicationic Hydrophobic Magnetic Ionic Liquids (13)

(14)

(15)

SEQUENCE LISTING

<160> NUMBER OF SEQ ID NOS: 7

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caccatgaca gtggtcccgg agaatttcgt ccc                                33

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgcctacag ttactgactt                                              20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgctgttcca gggacct                                                 17

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaattcggat ccggacgc                                                18

<210> SEQ ID NO 5
<211> LENGTH: 871
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (838)..(838)
<223> OTHER INFORMATION: a, c, t, g, unknown or other
<220> FEATURE:
<221> NAME/KEY: modified_base
<222> LOCATION: (844)..(846)
<223> OTHER INFORMATION: a, c, t, g, unknown or other
<220> FEATURE:

```
<221> NAME/KEY: modified_base
<222> LOCATION: (856)..(856)
<223> OTHER INFORMATION: a, c, t, g, unknown or other
<220> FEATURE:
<221> NAME/KEY: modified_base
<222> LOCATION: (859)..(871)
<223> OTHER INFORMATION: a, c, t, g, unknown or other

<400> SEQUENCE: 5
nnnnnnnnnn nntcaaattg gcatcattgg agntaccggc ctggatgatc cggaaatcct      60
ggaaggtcgc acagagaaat acgttgacac tccgttcggt aaaccgagcg atgccctgat     120
tatgggtaaa atcaaaaatg tcgactgcgt actcctggct cgtcacggtc gccagcacac     180
cattatgcct tccaaggtga attaccaggc caacatttgg gctctgaaag aggaagggtg     240
cacacacgtt atcgtgacaa cagcgtgcgg cagcctgcgt gaagaaatcc agccaggcga     300
tattgtcatt atcgaccagt ttattgaccg cacgacgatg cgcccgcagt ccttctacga     360
tggcagccat tcctgcgcgc gtggcgtatg ccacattcca atggccgaac cgttttgtcc     420
gaagacccgc gaggtattga ttgaaacagc gaaaaagctg ggtcttcgtt gccatagtaa     480
aggcaccatg gtaaccatcg aaggcccgcg tttctcttcc cgtgcggaga gcttcatgtt     540
tcgtacttgg ggcgctgacg taattaatat gacgactgtg cctgaagtag tgttggccaa     600
ggaggctggt atttgctatg cttccatcgc aatggcgacg gactacgact gttggaaaga     660
acacgaggaa gctgtgtccg tggaccgcgt gctgaagaca ctgaaagaaa atgccaacaa     720
agctaaatca ttactcttaa cgaccattcc ccagattggc tcgactgaat ggtcggaaac     780
cctccacaat ttgaaaaaca tggcgcagtt ctcggtcctg ctgccacgcc actgagcncg     840
ggannnccca aaattncann nnnnnnnnnn n                                    871

<210> SEQ ID NO 6
<211> LENGTH: 871
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(13)
<223> OTHER INFORMATION: a, c, t, g, unknown or other
<220> FEATURE:
<221> NAME/KEY: modified_base
<222> LOCATION: (15)..(17)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (838)..(838)
<223> OTHER INFORMATION: a, c, t, g, unknown or other
<220> FEATURE:
<221> NAME/KEY: modified_base
<222> LOCATION: (841)..(841)
<223> OTHER INFORMATION: a, c, t, g, unknown or other
<220> FEATURE:
<221> NAME/KEY: modified_base
<222> LOCATION: (845)..(847)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (858)..(871)
```

<223> OTHER INFORMATION: a, c, t, g, unknown or other

<400> SEQUENCE: 6

```
nnnnnnnnnn nnncnnntgg catcattgga nntaccggcc tggatgatcc ggaaatcctg    60
gaaggtcgca cagagaaata cgttgacact ccgttcggta aaccgagcga tgccctgatt   120
atgggtaaaa tcaaaaatgt cgactgcgta ctcctggctc gtcacggtcg ccagcacacc   180
attatgcctt ccaaggtgaa ttaccaggcc aacatttggg ctctgaaaga ggaagggtgc   240
acacacgtta tcgtgacaac agcgtgcggc agcctgcgtg aagaaatcca gccaggcgat   300
attgtcatta tcgaccagtt tattgaccgc acgacgatgc gcccgcagtc cttctacgat   360
ggcagccatt cctgcgcgcg tggcgtatgc cacattccaa tggccgaacc gttttgtccg   420
aagacccgcg aggtattgat tgaaacagcg aaaaagctgg ggtcttcgtt gccatagtaa   480
aggcaccatg gtaaccatcg aaggcccgcg tttctcttcc cgtgcggaga gcttcatgtt   540
tcgtacttgg ggcgctgacg taattaatat gacgactgtg cctgaagtag tgttggccaa   600
ggaggctggt atttgctatg cttccatcgc aatggcgacg gactacgact gttggaaaga   660
acacgaggaa gctgtgtccg tggaccgcgt gctgaagaca ctgaaagaaa atgccaacaa   720
agctaaatca ttactcttaa cgaccattcc ccagattggc tcgactgaat ggtcggaaac   780
cctccacaat ttgaaaaaca tggcgcagtt ctcggtcctg ctgccacgcc actgagcncg   840
naaannncca aattncannn nnnnnnnnnn n                                  871
```

<210> SEQ ID NO 7
<211> LENGTH: 884
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(8)
<223> OTHER INFORMATION: a, c, t, g, unknown or other
<220> FEATURE:
<221> NAME/KEY: modified_base
<222> LOCATION: (10)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (837)..(837)
<223> OTHER INFORMATION: a, c, t, g, unknown or other
<220> FEATURE:
<221> NAME/KEY: modified_base
<222> LOCATION: (841)..(842)
<223> OTHER INFORMATION: a, c, t, g, unknown or other
<220> FEATURE:
<221> NAME/KEY: modified_base
<222> LOCATION: (848)..(848)
<223> OTHER INFORMATION: a, c, t, g, unknown or other
<220> FEATURE:
<221> NAME/KEY: modified_base
<222> LOCATION: (856)..(884)
<223> OTHER INFORMATION: a, c, t, g, unknown or other

<400> SEQUENCE: 7

```
nnnnnnnncn nntcnaattg gcntcattgg aggtaccggc ctggatgatc cggaaatcct    60
```

-continued

```
ggaaggtcgc acagagaaat acgttgacac tccgttcggt aaaccgagcg atgccctgat    120
tatgggtaaa atcaaaaatg tcgactgcgt actcctggct cgtcacggtc gccagcacac    180
cattatgcct tccaaggtga attaccaggc caacatttgg gctctgaaag aggaagggtg    240
cacacacgtt atcgtgacaa cagcgtgcgg cagcctgcgt gaagaaatcc agccaggcga    300
tattgtcatt atcgaccagt ttattgaccg cacgacgatg cgcccgcagt ccttctacga    360
tggcagccat tcctgcgcgc gtggcgtatg ccacattcca atggccgaac cgttttgtcc    420
gaagacccgc gaggtattga ttgaaacagc gaaaaagctg ggtcttcgtt gccatagtaa    480
aggcaccatg gtaaccatcg aaggcccgcg tttctcttcc cgtgcggaga gcttcatgtt    540
tcgtacttgg ggcgctgacg taattaatat gacgactgtg cctgaagtag tgttggccaa    600
ggaggctggt atttgctatg cttccatcgc aatggcgacg gactacgact gttggaaaga    660
acacgaggaa gctgtgtccg tggaccgcgt gctgaagaca ctgaaagaaa atgccaacaa    720
agctaaatca ttactcttaa cgaccattcc ccagattggc tcgactgaat ggtcggaaac    780
cctccacaat ttgaaaaaca tggcgcagtt ctcggtcctg ctgccacgcc actgagntcg    840
nngtcccnaa aattannnnn nnnnnnnnnn nnnnnnnnnn nnnn    884
```

MAGNETIC IONIC LIQUIDS, METHODS OF MAKING AND USES THEREOF AS SOLVENTS IN THE EXTRACTION AND PRESERVATION OF NUCLEIC ACIDS

CROSS-REFERENCE TO RELATED APPLICATIONS

This application is a divisional application of U.S. Ser. No. 15/048,265 filed Feb. 19, 2016, now allowed, which claims priority to U.S. Provisional Application Ser. No. 62/118,901, filed under 35 U.S.C. § 111(b) on Feb. 20, 2015. The disclosures of all priority applications are incorporated herein by reference.

STATEMENT REGARDING FEDERALLY SPONSORED RESEARCH

This invention was made with government support under Grant Number CHE-1413199 awarded by the National Science Institute. The government has certain rights in this invention.

SEQUENCE LISTING

The instant application contains a Sequence Listing which has been submitted via EFS-web and is hereby incorporated by reference in its entirety. The ASCII copy, created on Feb. 18, 2016, is named 420_56859_SEQ_LIST_D2014-41.txt, and is 7,113 bytes in size.

```
                                           [SEQ ID NO: 1]
5'-CAC CAT GAC AGT GGT CCC GGA GAA TTT CGT CCC-3'

[SEQ ID NO: 2]
5'-ATG CCT ACA GTT ACT GAC TT-3'

[SEQ ID NO: 3]
5'-TGC TGT TCC AGG GAC CT-3'

[SEQ ID NO: 4]
5'-GAA TTC GGA TCC GGA CGC-3'
```

FIELD OF THE INVENTION

This disclosure describes magnetic ionic liquids having a cationic component and an anionic component, where at least one of the cationic components and the anionic components is a paramagnetic component. The magnetic ionic liquid is capable of manipulation by an external magnetic field.

BACKGROUND OF THE INVENTION

Ionic liquids (ILs) are molten organic salts composed of organic cations and inorganic/organic anions with low melting points (≤100° C.). These solvents have garnered much attention due to their low vapor pressure at ambient temperatures, high thermal stability, wide electrochemical window, and multiple solvation capabilities.

The analysis of deoxyribonucleic acid (DNA) plays a central role in a variety of applications ranging from the determination of microbial diversity in environmental samples, identifying pathogens in food, monitoring the levels of cell free nucleic acids in cancer prognosis (liquid biopsies), bioprospecting, and phylogenetic studies. Techniques such as polymerase chain reaction (PCR) and DNA sequencing enable the analysis of extremely small quantities of DNA. However, the reliability and reproducibility of these methods largely depends on the quality of the sample. Complex environmental and biological samples often contain compounds such as humic acids, proteins, or lipids that can inhibit PCR amplification or DNA sequencing reactions. In these circumstances, a proper sample preparation technique is necessary to purify and preconcentrate DNA for accurate and reproducible analysis.

Various sample preparation techniques have been developed for DNA purification including phenol-chloroform alkaline extraction, cesium chloride-based density gradient ultracentrifugation, and solid phase extraction (SPE) methods. Although useful in many cases, these conventional DNA purification approaches often involve large sample volumes, the use of organic solvents, time-consuming and laborious centrifugation steps, or multiple sample transfer steps that increase the risk of contamination. DNA extraction based on commercial SPE kits reduces the volume of organic solvent consumed as well as the time required for analysis, but the cost per sample remains high and the number of extractions that can be performed is limited. In some cases, the yield and purity of DNA obtained using different commercial extraction kits can be highly variable. Consequently, new methods that address the deficiencies of existing DNA sample preparation techniques are particularly desirable.

SUMMARY OF THE INVENTION

Described herein are magnetic ionic liquids that have at least one cationic component and at least one anionic component. At least one of the cationic components or at least one of the anionic components is a paramagnetic component. The magnetic ionic liquid being capable of manipulation by an external magnetic field.

In certain embodiments, the cationic component is monocationic, dicationic or tricationic. Also, n certain embodiments, the cationic component is an asymmetric cationic component.

In certain embodiments, the magnetic ionic liquid comprises multiple magnetic iron(III) centers. Also, in certain embodiments, the paramagnetic component comprises a high spin transition metal. In one embodiment, the paramagnetic component comprises a high-spin $d^5$ iron(III) center. For example, in certain embodiments, wherein the ionic liquid has an effective magnetic moment of up to 11.76 Bohr magnetons.

In certain embodiments, the magnetic ionic liquid comprises one or more of: benzyl substituents; dysprosium; a benzimidazolium cation; an imidazolium cation.

In certain embodiments, the anionic component comprises three anions.

In certain embodiments, the anionic component is selected from: a [FeCl$_3$Br$^-$] anion and a [NTf$_2^-$] anion.

Also described herein is a method of increasing the effective magnetic moment of an ionic liquid, comprising: incorporating an additional iron(III) center into an ionic liquid, and thereby increasing the effective magnetic moment of the ionic liquid. In certain embodiments, the method comprises using one or more steps shown in Scheme 1a or Scheme 1b; Scheme 2; Scheme 3; or Scheme 4.

The magnetic ionic liquids are useful in conducting gas chromatography, where the magnetic ionic liquid is used as a stationary phase.

The magnetic ionic liquids are useful in conducting nucleic acid extraction, where the magnetic ionic liquid is used as a solvent to extract a nucleic acid from an aqueous solution; and, optionally, subjecting the extracted nucleic acid to a polymerase chain reaction (PCR) process.

In certain embodiment, the nucleic acid comprises DNA, or a synthetic DNA.

In certain embodiments, the method comprises dispersive liquid-liquid microextraction.

In certain embodiments, the method is single droplet extraction, or a dispersive droplet extraction.

In certain embodiments, the method comprises conducting solid-phase microextraction using the magnetic ionic liquid as sorbent coating immobilized on a solid support to extract DNA from a solution.

Various aspects of this invention will become apparent to those skilled in the art from the following detailed description of the preferred embodiment, when read in light of the accompanying drawings.

BRIEF DESCRIPTION OF THE FIGURES

The patent or application file contains one or more drawings executed in color and/or one or more photographs. Copies of this patent or patent application publication with color drawing(s) and/or photograph(s) will be provided by the U.S. Patent and Trademark Office upon request and payment of the necessary fees.

(FIG. 10A) $[(C_{16}BnIM)_2C_{12}^{2+}][NTf2-, FeCl_3Br—]$, (FIG. 10B) $[P_{6,6,6,14+}][FeCl_4—]$, and (FIG. 10C) $[(C_8)_3BnN+][FeCl_3Br—]$. Diamonds (◇) represent extraction efficiency values of stDNA, and circles (○) denote extraction efficiencies of protein.

DETAILED DESCRIPTION OF THE INVENTION

Definitions

Figure 1A:
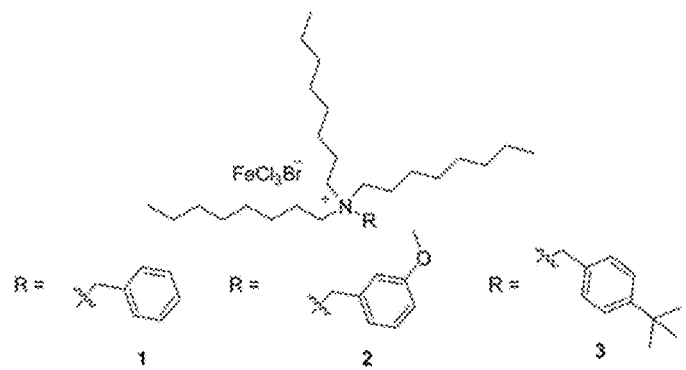
FIG. 1A: Chemical structures of the three classes of hydrophobic magnetic ionic liquids (MILs): monocationic, dicationic and tricationic.
Figure 1A:
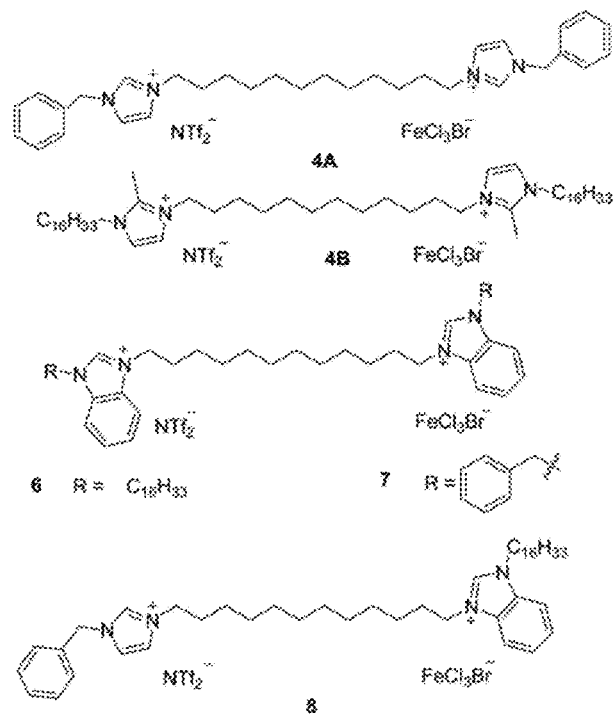
Figure 1A:
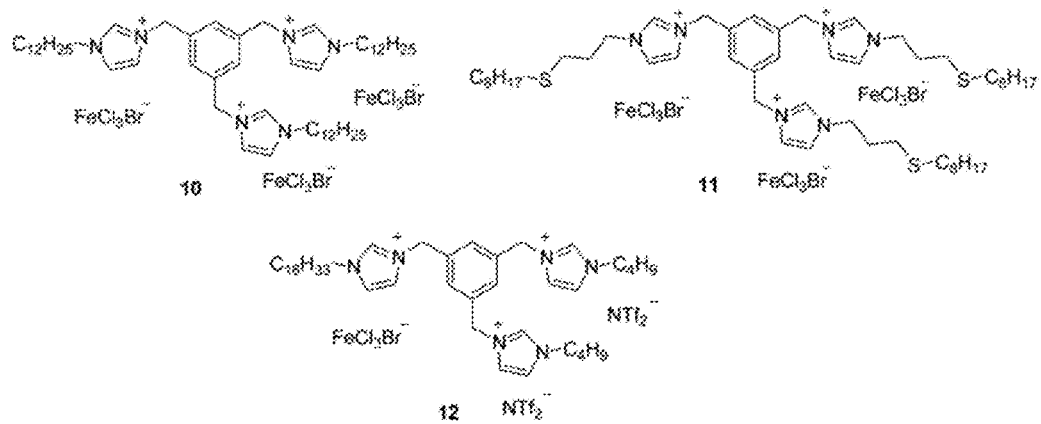

It must be noted that as used herein and in the appended claims, the singular forms "a," "an," and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising," "including," and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art. Although any methods and materials similar or equivalent to those described herein can be used in the practice or testing of the present disclosure, the preferred methods and materials are now described.

Every formulation or combination of components described or exemplified herein can be used to practice the materials and methods disclosed herein, unless otherwise stated.

When a group of substituents is disclosed herein, it is understood that all individual members of that group and all subgroups, including any isomers and enantiomers of the group members, are disclosed separately. When a Markush group or other grouping is used herein, all individual members of the group and all combinations and subcombinations possible of the group are intended to be individually included in the disclosure. It is intended that any one or more members of any Markush group or listing provided in the specification can be excluded if desired. When a compound is described herein such that a particular isomer or enantiomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Specific names of compounds are intended to be exemplary, as it is known that one of ordinary skill in the art can name the same compounds differently.

Thus, as used herein, the term "alkyl" includes straight, branched and cyclic alkyl groups, having up to 10 carbon atoms. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms. Non-limiting examples of alkyl groups include n-propyl, isopropyl, and isobutyl groups.

Illustrative aliphatic groups thus include, but are not limited to, for example, methyl, ethyl, n-propyl, isopropyl, cyclopropyl, —CH$_2$-cyclopropyl, allyl, n-butyl, secbutyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl-n, hexyl, sec-hexyl, cyclohexyl, —CH$_2$cyclohexyl moieties and the like, which again, can bear one or more substituents. Illustrative alkynyl groups include, but are not limited to, for example propargyl.

"Aryl" refers to an unsaturated aromatic or heteroaromatic carbocyclic group of from 1 to 15 carbon atoms having a single ring (e.g. phenyl) or multiple condensed rings (e.g., naphthyl or anthryl). Preferred aryls include substituted aromatic C6-12 carbocycle; unsubstituted aromatic C1-10 heterocycle; substituted aromatic C1-10 heterocycle; wherein when substituted, the substitution is —XR.

Aralkyl refers to an alkyl connected to an aryl.

Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like.

"Halogen" refers to fluoro, chloro, bromo and iodo and preferably is either chloro or bromo.

"Heterocycle" or "heterocyclic" refers to a saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, aminoacyl, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsynumetric di-substituted amines having different substituents selected from alkyl, substituted alkyl, aryl, heteroaryl and heterocyclic, and the like. Such heterocyclic groups can have a single ring or multiple condensed rings. Preferred saturated heterocyclics include morpholino, piperidinyl, and the like; and preferred unsaturated heterocycles include pyridyl and the like.

It will be appreciated by one of ordinary skill in the art that asymmetric centers can exist in the compounds of the present disclosure. Thus, the compounds and pharmaceutical compositions thereof can be in the form of an individual enantiomer, diastereomer or geometric isomer, or can be in the form of a mixture of stereoisomers. It is to be understood that the present disclosure encompasses all possible isomers such as geometric isomers, optical isomers, stereoisomers and tautomers based on an asymmetric carbon, which can occur in the structures of the compounds, and mixtures of such isomers and compositions comprising those compounds, and is not limited to the specific stereochemistry shown for the compounds disclosed in the present specification. It will be further appreciated that the absolute stereochemistry of some of the compounds recited in the Exemplification herein cannot have been determined, and that when a stereochemistry was assigned for those compounds it is meant to be tentative and to indicate that a set of diastereomers exists for those compounds and/or that a diastereomer was isolated in pure form. Furthermore, it will be appreciated that certain of the compounds disclosed herein contain one or more double bonds and these double bonds can be either Z or E, unless otherwise indicated. In certain embodiments, the compounds of the present disclosure are enantiopure compounds. In certain other embodiments, mixtures of stereoisomers or diastereomers are provided.

Furthermore, this disclosure is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

General Description

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

Example 1

Synthesis of Hydrophobic Magnetic Ionic Liquids

In an effort to demonstrate the hydrophobicity and magnetic susceptibility in MILs, novel hydrophobic MILs were synthesized.

Figure 1B:
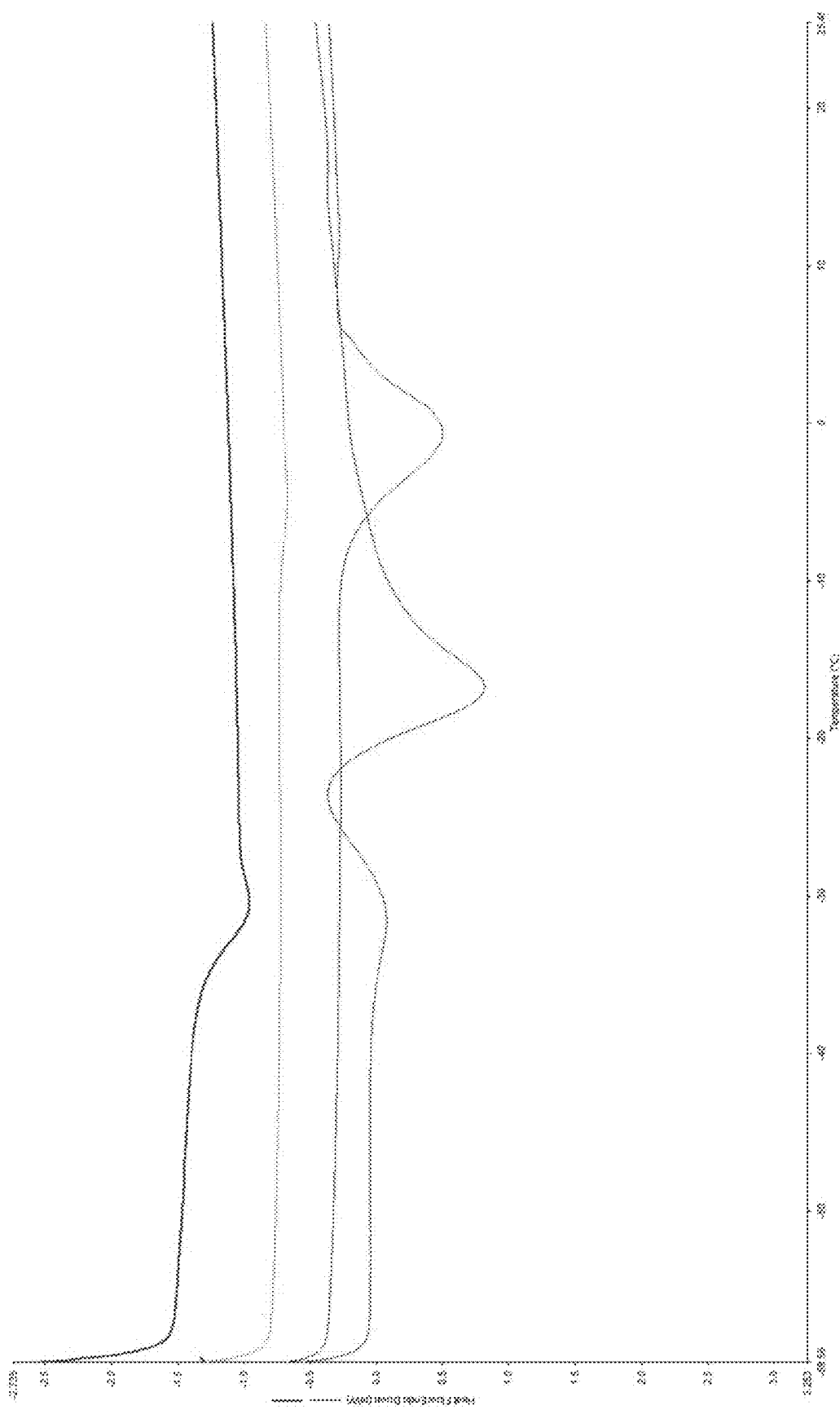
FIG. 1B-FIG. 1C: The thermal properties of the MILs were evaluated using thermal gravimetric analysis (TGA) (FIG. 1C), and differential scanning calorimetry (DSC) (FIG. 1B).
Figure 1C:
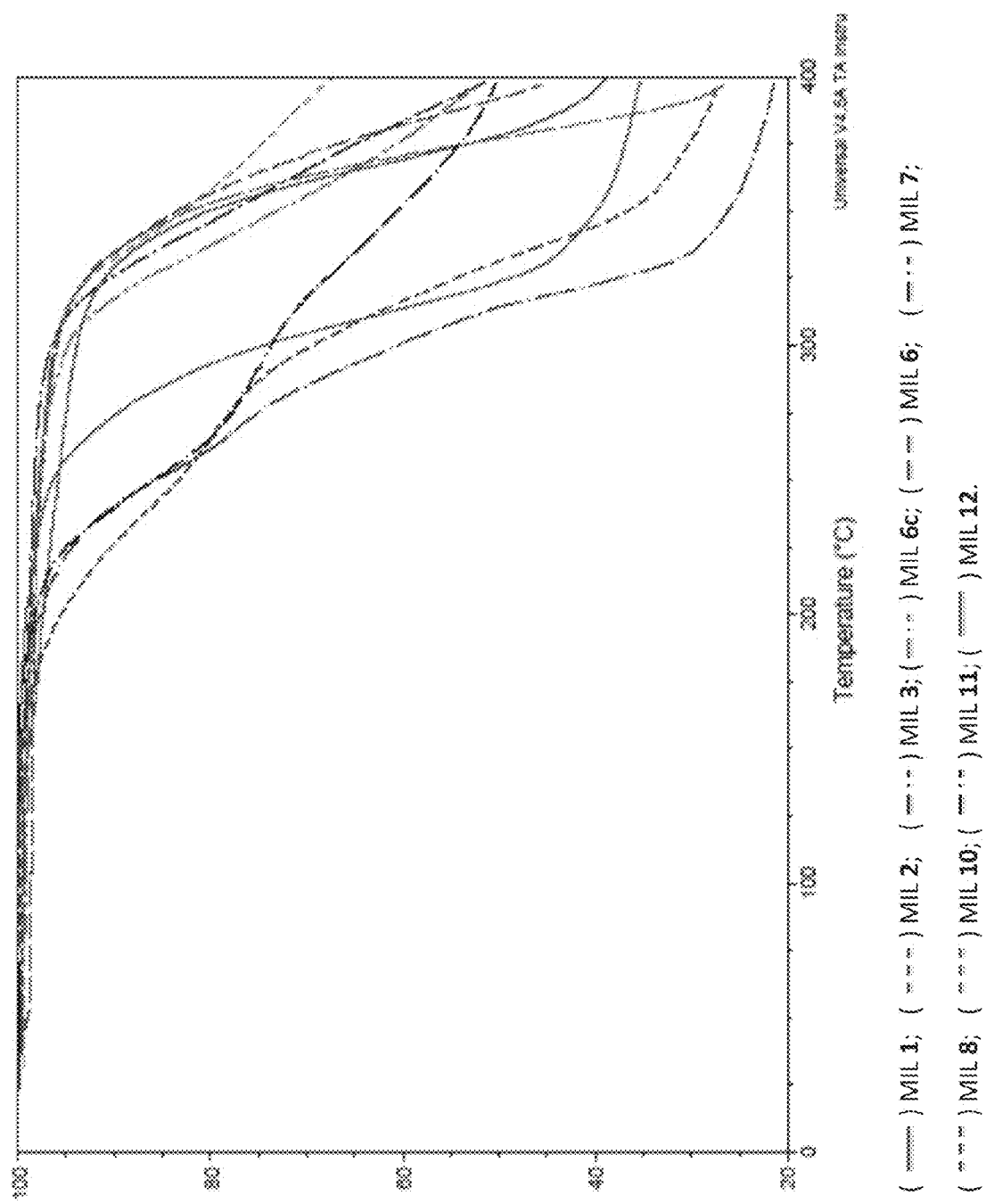

FIG. 1A groups the MILs into the following three classes: monocationic ammonium-based MILs (1-3), symmetrical/unsymmetrical dicationic MILs with heteroanions (4a, 4b, and 6-8), and symmetrical/unsymmetrical tricationic MILs (10-12). Each synthetic route undertaken offers a unique approach toward incorporating hydrophobicity and magnetic susceptibility to the MIL structure. By designing MILs with multiple paramagnetic iron(III) centers, high effective magnetic moments ($\mu_{eff}$) were achieved. The tricationic MIL 12 exhibited an $\mu_{eff}$ of 11.76 Bohr magnetons ($\mu B$), which is a very high $\mu_{eff}$ for a MIL. Moreover, the low water solubilities observed for the MILs (less than 0.25% (w/v)) are ideal for employing these compounds in magnet-based aqueous biphasic systems. The thermal properties of each MIL were evaluated using thermal gravimetric analysis (TGA) (FIG. 1C) and differential scanning calorimetry (DSC) (FIG. 1B).

Materials and Measurements

Imidazole (99%), 2-methylimdazole (99%), benzimidazole (98%), trioctylamine (97%), benzyl bromide (98%), 3-methoxybenzene (98%), 4-(tert-butyl)benzene (97%), octanethiol (≥98.5%), 2.2-dimethoxy-2-phenylacetophenone (99%), lithium bis(trifluoromethyl)sulfonylimide, and 1,12-dibromododecane (98%) were purchased from Acros Organics (Morris Plains, N.J., USA).

Acetonitrile, chloroform, dichloromethane, methanol, and diethyl ether were purchased from Fisher Scientific (Fair Lawn, N.J., USA). Deuterated chloroform and dimethyl sulfoxide (DMSO) were obtained from Cambridge Isotope Laboratories (Andover, Mass., USA). The NMR solvents were used as received without additional drying. Iron(III) chloride hexahydrate ($FeCl_3 \cdot 6H_2O$) (97%), 1-bromohexadecane (99%), 1-bromododecane (99%), 1,3,5-tris(bromomethyl)benzene (97%), and dimethyl sulfoxide were purchased from Sigma-Aldrich (St. Louis, Mo., USA). All reagents were used as received without any further purification.

$^1H$ NMR and $^{13}C$ NMR spectra were recorded using a Varian 400 MHz nuclear magnetic resonance spectrometer. Chemical shifts reported herein are relative to tetramethylsilane. Mass spectra were obtained using an Esquire-LC-MS/MS from Bruker Daltonics. Thermogravimetric analyses were performed using a TA Instruments TGA Q600 thermogravimetric analyzer. All samples were loaded in platinum pans and heated at a rate of 5° C. min-1 under nitrogen flow (50 mL min-1). Differential scanning calorimetry (DSC) traces were obtained using a Diamond differential scanning calorimeter from PerkinElmer. Magnetic susceptibility measurements were determined using a magnetic susceptibility balance (MSB) from Johnson Matthey. The MSB was calibrated with $CuSO_4 \cdot 5H_2O$ and validated using the data for the [$P_{6,6,6,14+}$][$FeCl_4-$] MIL. Visible absorption spectra were obtained using a Thermo Scientific Evolution 300 UV-vis spectrophotometer. Absorption spectra of MILs were collected using acetonitrile as the solvent.

Synthesis of Monocationic Hydrophobic MILs

Figure 2A:
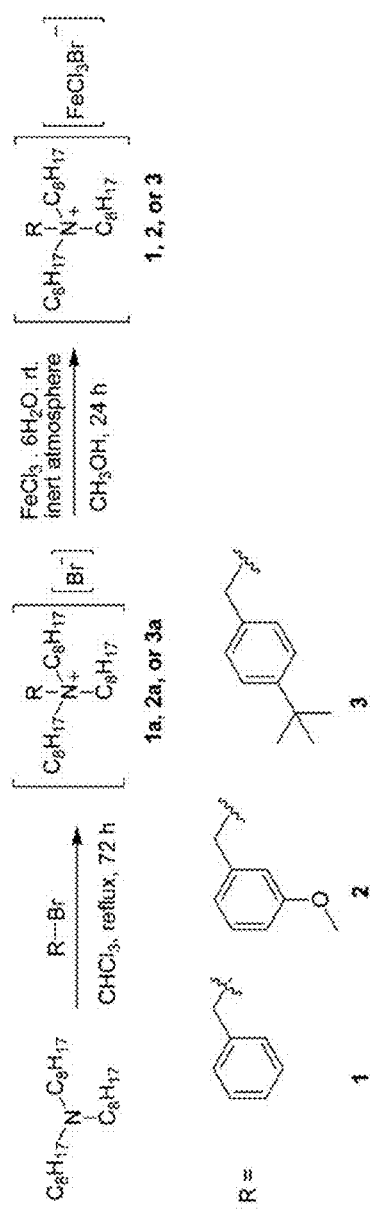
FIG. 2A: Scheme 1a, showing synthesis of monocationic and dicationic hydrophobic magnetic ionic liquids 1, 2 and 3 (MILs).

As shown in FIG. 2—Scheme 1, the synthesis of MILs 1-3 involves the reaction of trioctylamine (1 mmol) with bromomethyl substituents (R—CH2Br; R=benzene, methoxybenzene, and tert-butylbenzene; 1.1 mmol) in chloroform (25 mL) for 72 h under reflux conditions. The solvent was evaporated under reduced pressure followed by washing the crude compound with hexanes (4×25 mL) under sonication to remove the unreacted starting materials. The bromide salt was then dried under vacuum at 60° C. for 12 h. Characterization of compounds 1a-3a was performed using $^1H$ NMR, $^{13}C$ NMR, and ESI-MS. After confirming the purity of the intermediates, compounds 1a-3a were reacted with equimolar amounts of $FeCl_3 \cdot 6H_2O$ in methanol at room temperature under nitrogen atmosphere for 4 h. After evaporation of solvent, the crude MIL was washed with an excess of deionized water to remove unreacted $FeCl_3$ from the final product. The MILs 1-3 were then dried under vacuum at 80° C. for 48 h and characterized using visible spectrophotometry and elemental analysis.

Characterization of 1a

Yield 92%. $^1$H NMR (400 MHz; CDCl$_3$; ppm): δ0.86 (t, JH—H=6.35 Hz, 9H); 1.25 (m, 30H); 1.75 (m, 6H); 3.29 (t, JH—H=8.06 Hz, 6H); 4.92 (s, 2H); 7.42 (m, 3H); 7.53 (m, 2H). $^{13}$C NMR (400 MHz; CDCl$_3$; ppm): δ14.31; 22.81; 22.97; 26.61; 29.28; 31.84; 59.08; 63.51; 127.68; 129.60; 130.97; 132.76.

Characterization of MIL 1

Yield 91%. A dark reddish-brown viscous liquid. Characteristic bands for [FeCl$_3$Br—] anion were observed at 534, 619, and 688 nm using visible spectroscopy. Elem. Anal. Calcd (%) for C$_{31}$H$_{58}$BrCl$_3$FeN (686.91): C, 54.21; H, 8.51; N, 2.04. Found: C, 53.67; H, 8.06; N, 1.56.

Characterization of 2a

Yield 93%. $^1$H NMR (400 MHz; CDCl$_3$; ppm): δ0.89 (t, JH—H=6.35 Hz, 9H); 1.25 (m, 30H); 1.75 (m, 6H); 3.33 (t, JH—H=8.42 Hz, 6H); 3.86 (s, 3H); 4.89 (s, 2H); 7.22 (m, 3H); 7.35 (m, 1H). $^{13}$C NMR (400 MHz; CDCl$_3$; ppm); δ14.41; 22.90; 23.08; 26.72; 29.41; 31.93; 56.05; 59.28; 63.62; 116.71; 118.41; 124.61; 129.05; 130.62; 160.61.

Characterization of MIL 2

Yield 91%. A dark reddish-brown viscous liquid. Visible spectroscopy showed characteristic bands for the [FeCl$_3$Br—] at 534, 619, and 688 nm. Elem. Anal. Calcd (%) for C$_{32}$H$_{60}$BrCl$_3$FeNO (716.93): C, 53.61; H, 8.44; N, 1.95. Found: C, 54.41; H, 7.64; N, 1.31.

Characterization of 3a

Yield 89%. $^1$H NMR (400 MHz; CDCl$_3$; ppm): δ0.88 (t, JH—H=6.23 Hz, 9H); 1.32 (m, 39H); 1.75 (m, 6H); 3.30 (t, JH—H=8.06 Hz, 6H); 4.82 (s, 2H); 7.44 (m, 4H). $^{13}$C NMR (400 MHz; CDCl$_3$; ppm): δ14.32; 22.81; 22.94; 26.62; 29.30; 29.36; 31.36; 31.87; 58.86; 63.12; 124.33; 126.61; 132.38; 154.50.

Characterization of MIL 3

Yield 95%. A dark reddish-brown viscous liquid. Characteristic bands for [FeCl$_3$Br—] anion were observed at 534, 619, and 688 nm using visible spectroscopy. Elem. Anal. Calcd (%) for C$_{35}$H$_{66}$BrCl$_3$FeN (743.01): C, 56.58; H, 8.95; N, 1.89. Found: C, 57.38; H, 8.35; N, 1.62.

Synthesis of Compound 5

Figure 2B:
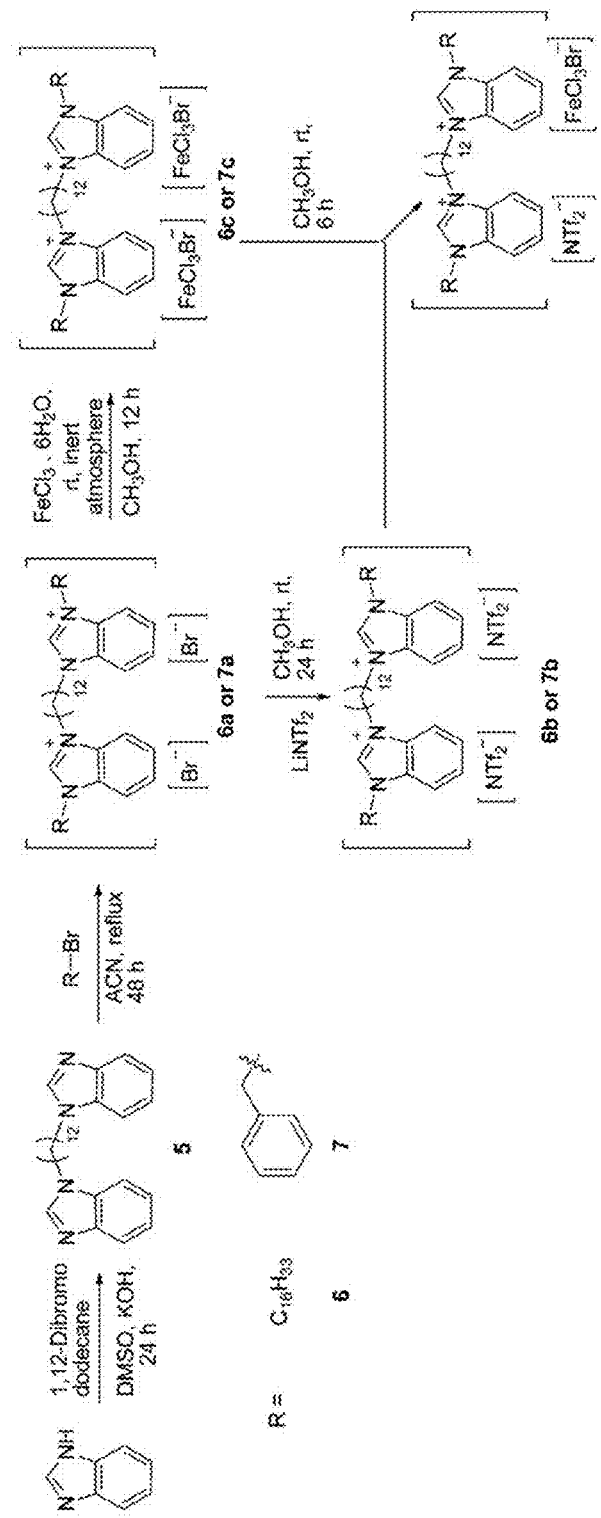
FIG. 2b: Scheme 1b, showing synthesis of monocationic and dicationic hydrophobic magnetic ionic liquids 6 and 7 (MILs).

Compound 5 was synthesized as shown in FIG. 2B—Scheme 1b. Benzimidazole (2.00 g, 17.0 mmol) and potassium hydroxide (2.01 g, 35.0 mmol) were dissolved in dimethyl sulfoxide (30 mL) and stirred for 6 h at room temperature. Then, 1,12-dibromododecane (2.80 g, 8.53 mmol) was added and continuously stirred for 24 h. Water (30 mL) was added to the reaction mixture, and the contents were subsequently transferred to a separatory funnel. The reaction mixture was then extracted with chloroform (4×40 mL). The organic phases were washed several times with water until the aqueous phase was a neutral pH. The organic phases were then collected and dried over anhydrous sodium sulfate. After evaporation of the solvent, compound 5 was dried at 70° C. under reduced pressure for 12 h.

Characterization of 5

Yield 80-83%. $^1$H NMR (400 MHz; DMSO; ppm): δ1.14 (m, 16H); 1.75 (m, 4H); 4.21 (t, JH—H=6.84 Hz, 4H); 7.18 (m, 2H); 7.23 (m, 2H); 7.58 (m, 2H); 7.65 (m, 2H); 8.22 (s, 2H). $^{13}$C NMR (400 MHz; DMSO; ppm): δ26.07; 28.47; 28.83; 29.35; 44.04; 110.41; 110.41; 119.38; 119.45; 121.32; 122.19; 133.75; 143.46; 144.04.

Synthesis of Benzimidazolium-Containing Dicationic Heteroanion-Based MILs

The synthesis of MILs 6 and 7 is shown in FIG. 2B—Scheme 1b. To a stirred solution of compound 5 (1.24 mmol) in acetonitrile (15 mL), hexadecyl/benzyl bromide (2.60 mmol) was added and stirred at reflux for 48 h. The solvent was evaporated under reduced pressure, and the crude compound 6a/7a was washed with an excess of diethyl ether (4×20 mL) using sonication. The dicationic bromide salt (6a/7a) was then dried at 80° C. under reduced pressure for 6 h to remove the residual solvent from the product. Compounds 6b and 7b were prepared by reacting 6a/7a (1 mmol) with lithium bisRtrifluoromethylisulfonyllimide (2.2 mmol) in methanol at room temperature for 24 h. After solvent evaporation, the crude compounds were washed with an excess of water and the halide impurities monitored by adding silver nitrate to the aqueous phase.

Compounds 6c and 7c were obtained by reacting 6b/7b (1 mmol) with FeCl$_3$.6H$_2$O (1.2 mmol) in methanol at room temperature under nitrogen atmosphere for 12 h. The solvent was evaporated and the compounds were washed with water (4×10 mL) under sonication to remove unreacted iron chloride. Compounds 6c/7c were dried under vacuum at 80° C. for 16 h to remove residual water.

Heteroanion-based MILs (6 and 7) were synthesized by mixing 6c or 7c (1 mmol) with 6b or 7b (1 mmol), respectively, in methanol for 6 h at room temperature.

Characterization of 6a

Yield 91%. $^1$H NMR (400 MHz; CDCl$_3$; ppm): δ0.82 (t, JH—H=6.32 Hz, 6H); 1.18 (m, 68H); 2.01 (m, 8H); 4.60 (m, 8H); 7.74 (m, 8H); 11.33 (s, 2H). $^{13}$C NMR (400 MHz; CDCl$_3$; ppm): δ14.17; 22.71; 26.41; 29.68; 29.70; 31.94; 47.71; 113.13; 113.32; 127.20; 131.29; 131.30; 142.51. ESI-MS: m/2z (+) 426.7.

Characterization of 6b

Yield 87%. $^1$H NMR (400 MHz; CDCl$_3$; ppm): δ0.87 (t, JH—H=6H); 1.25 (m, 68H); 1.98 (m, 8H); 4.48 (m, 8H); 7.74 (m, 8H); 9.42 (s, 2H). $^{13}$C NMR (400 MHz; CDCl$_3$; ppm): δ14.40, 22.96; 26.39; 26.69; 29.07; 29.74; 29.95; 32.19; 48.05; 113.33; 113.60; 127.68; 127.76; 131.61; 141.09. ESI-MS: m/2z (+) 426.7; m/z (−) 279.1.

Characterization of MIL 6

Yield 91%. The presence of the paramagnetic anion, [FeCl$_3$Br—], was confirmed using visible spectroscopy. Elem. Anal. Calcd (%) for C$_{60}$H$_{100}$BrCl$_3$F$_6$FeN$_5$O$_4$S$_2$ (1375.7): C, 52.38; H, 7.33; N, 5.09. Found: C, 53.28; H, 7.30; N, 5.06.

Characterization of 7a

Yield 92%. $^1$H NMR (400 MHz; DMSO; ppm): δ1.21 (m, 16H); 1.92 (m, 4H); 4.52 (t, JH—H=7.14 Hz, 4H); 5.80 (s, 4H); 7.39 (m, 6H); 7.52 (m, 4H); 7.66 (m, 4H); 7.97 (m, 2H); 8.11 (m, 2H); 10.10 (s, 2H). $^{13}$C NMR (400 MHz; DMSO; ppm): δ25.82; 28.45; 28.49; 28.94; 46.84; 49.83; 113.90; 126.64; 128.23; 128.96; 131.29; 134.12; 142.38. ESI-MS: m/2z (+) 292.4.

Characterization of 7b

Yield 90%. $^1$H NMR (400 MHz; CDCl$_3$; ppm): δ1.24 (m, 16H); 1.99 (m, 4H); 4.48 (t, JH—H=7.32 Hz, 4H); 5.63 (s, 4H); 7.36 (m, 10H); 7.59 (m, 2H); 7.62 (m, 4H); 7.76 (m, 2H); 9.44 (s, 2H). $^{13}$C NMR (400 MHz; CDCl$_3$; ppm): δ26.29; 28.67; 29.01; 29.26; 48.01; 51.56; 113.41; 113.92; 118.33; 121.52; 121.67; 128.22; 129.57; 132.38; 140.90. ESI-MS: m/2z (+) 292.4; m/z (−) 279.1.

Characterization of MIL 7

Yield 88%. A dark brown viscous liquid. Characteristic bands for the [FeCl$_3$Br—] anion were observed at 534, 619, and 688 nm using visible spectroscopy. Elem. Anal. Calcd (%) for C$_{42}$H$_{48}$BrCl$_3$F$_6$FeN$_5$O$_4$S$_2$ (1107.09): C, 45.57; H, 4.37; N, 6.33. Found: C, 45.93; H, 4.14; N, 6.35.

Synthesis of MIL 8

Figure 3:
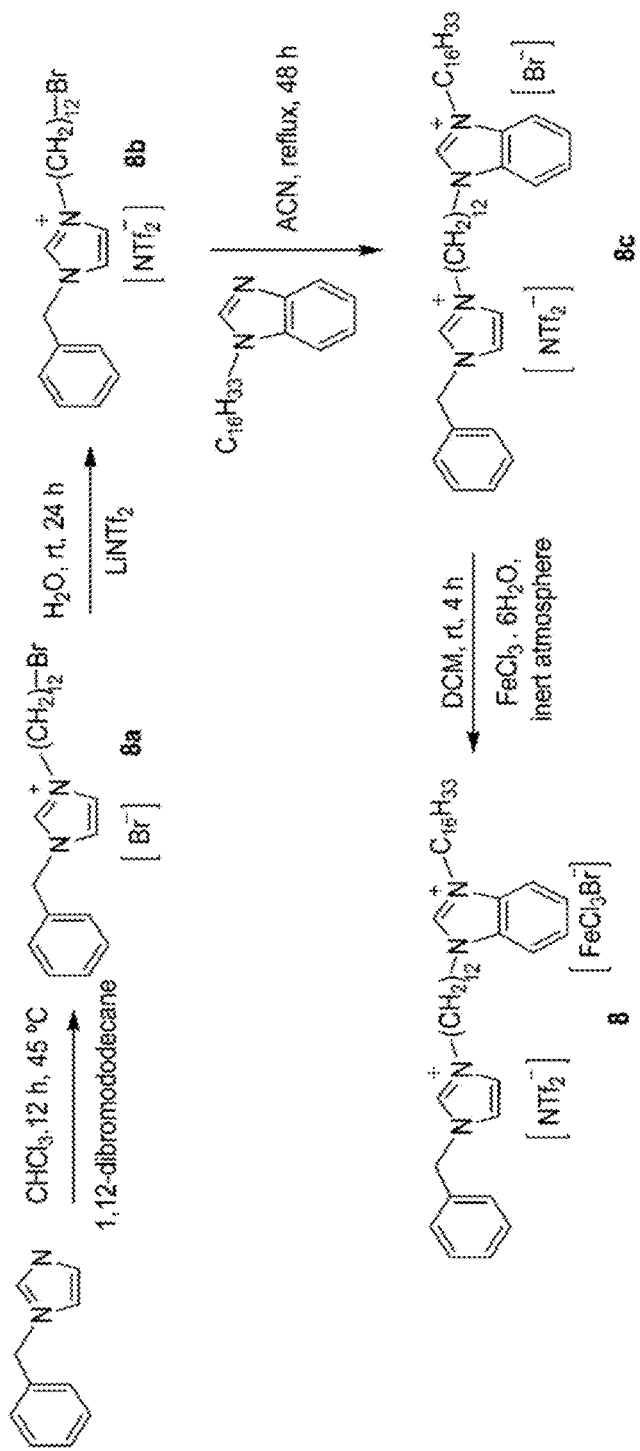
FIG. 3: Scheme 2, showing synthesis of dicationic heterocation-based hydrophobic magnetic ionic liquids (MILs).

As shown in FIG. 3—Scheme 2, compound 8 was synthesized. Briefly, a solution of 1,12-dibromododecane (8.20 g, 25.0 mmol in 30 mL of chloroform) was added dropwise using a syringe to a stirred solution of N-benzylimidazole (1.00 g, 6.32 mmol) in chloroform (40 mL) for 2 h. The reaction mixture was allowed to stir for 12 h under reflux. The crude compound 8a was obtained by evaporating the solvent under reduced pressure and washed with excess of hexanes and ethyl acetate (1:1; 3×30 mL) under sonication to remove the unreacted starting materials. Compound 8a was dried in vacuum at 70° C. for 16 h to remove the residual solvents. Compound 8b was obtained by anion exchange of 8a with LiNTf2 in water at room temperature for 24 h. After drying, compound 8b (0.30 g, 0.43 mmol) was reacted with previously synthesized 1-hexadecylbenzimidazole (0.153 g, 0.450 mmol) in acetonitrile under reflux for 48 h. The resulting crude compound 8c was washed with an excess of diethyl ether under sonication and dried under reduced pressure at 70° C. for 24 h. Finally, 8c (1 mmol) was reacted with $FeCl_3·6H_2O$ (1.1 mmol) in dichloromethane at room temperature for 6 h to yield crude compound 8. After evaporation of the solvent, compound 8 was washed several times with water to remove the unreacted iron chloride and dried under vacuum for 4 h at 70° C.

Characterization of 8b

Yield 65%. $^1$H NMR (400 MHz; DMSO; ppm): δ1.23 (m, 16H); 1.78 (m, 4H); 3.52 (t, JH—H=6.59 Hz, 2H); 4.16 (t, JH—H=6.96 Hz, 2H); 5.41 (s, 2H); 7.41 (m, 5H); 7.81 (m, 2H); 9.29 (s, 1H). $^{13}$C NMR (400 MHz; DMSO; ppm): δ26.17; 28.19; 28.79; 28.99; 29.49; 29.55; 29.90; 32.89; 35.95; 49.64; 52.63; 123.28; 123.49; 128.87; 129.69; 136.79. ESI-MS: m/z (+) 407.3.

Characterization of 8c

Yield 82%. $^1$H NMR (400 MHz; DMSO; ppm): δ0.84 (t, JH—H=6.59 Hz, 3H); 1.21 (m, 42H); 1.76 (m, 2H); 1.89 (m, 4H); 4.15 (t, JH—H=6.96 Hz, 2H); 4.48 (t, JH—H=6.59 Hz, 4H); 5.41 (s, 2H); 7.40 (m, 5H); 7.70 (m, 2H); 7.82 (m, 3H); 8.11 (m, 2H); 9.29 (s, 1H); 9.80 (s, 1H). $^{13}$C NMR (400 MHz; DMSO; ppm): δ13.98; 22.13; 25.58; 25.72; 25.82; 28.43; 29.06; 29.31; 31.32; 46.69; 48.89; 51.98; 113.74; 122.61; 122.80; 126.57; 128.21; 129.01; 131.10; 134.48; 136.10; 142.04. ESI-MS: m/2z (+) 334.7; m/z (−) 279.1.

Characterization of MIL 8

Yield 91%. A dark brown viscous liquid. Characteristic bands for the [$FeCl_3Br$—] anion were observed at 534, 619, and 688 nm using visible spectroscopy. Elem. Anal. Calcd (%) for $C_{47}H_{72}BrCl_3F_6FeN_5O_4S_2$ (1191.33): C, 47.38; H, 6.09; N, 5.88. Found: C, 47.85; H, 6.17; N, 6.07.

Synthesis of Compound 9

Briefly, imidazole (0.59 g, 8.68 mmol) and potassium hydroxide (2.09 9, 36.96 mmol) were dissolved in DMSO (30 mL) and stirred for 12 h at room temperature. Compound 9 was then obtained by adding 1,3,5-tris(bromomethyl)benzene (1 g, 2.80 mmol) to the reaction flask and stirring for 12 h. Water (30 mL) was added and the reaction mixture subsequently transferred to a separatory funnel and extracted with chloroform (4×30 mL). The organic phases were washed several times with water and dried over anhydrous sodium sulfate. After evaporation of the solvent under reduced pressure, compound 9 was dried at 70° C. for 6 h.

Characterization of 9

Yield 70-75%. $^1$H NMR (400 MHz; CDCl$_3$; ppm): δ5.08 (s, 6H); 6.84 (m, 6H); 7.12 (s, 3H); 7.52 (s, 3H). $^{13}$C NMR (400 MHz; CDCl$_3$; ppm): δ50.37; 119.40; 125.77; 130.45; 137.61; 138.65.

Synthesis of Compound 10

Figure 4:
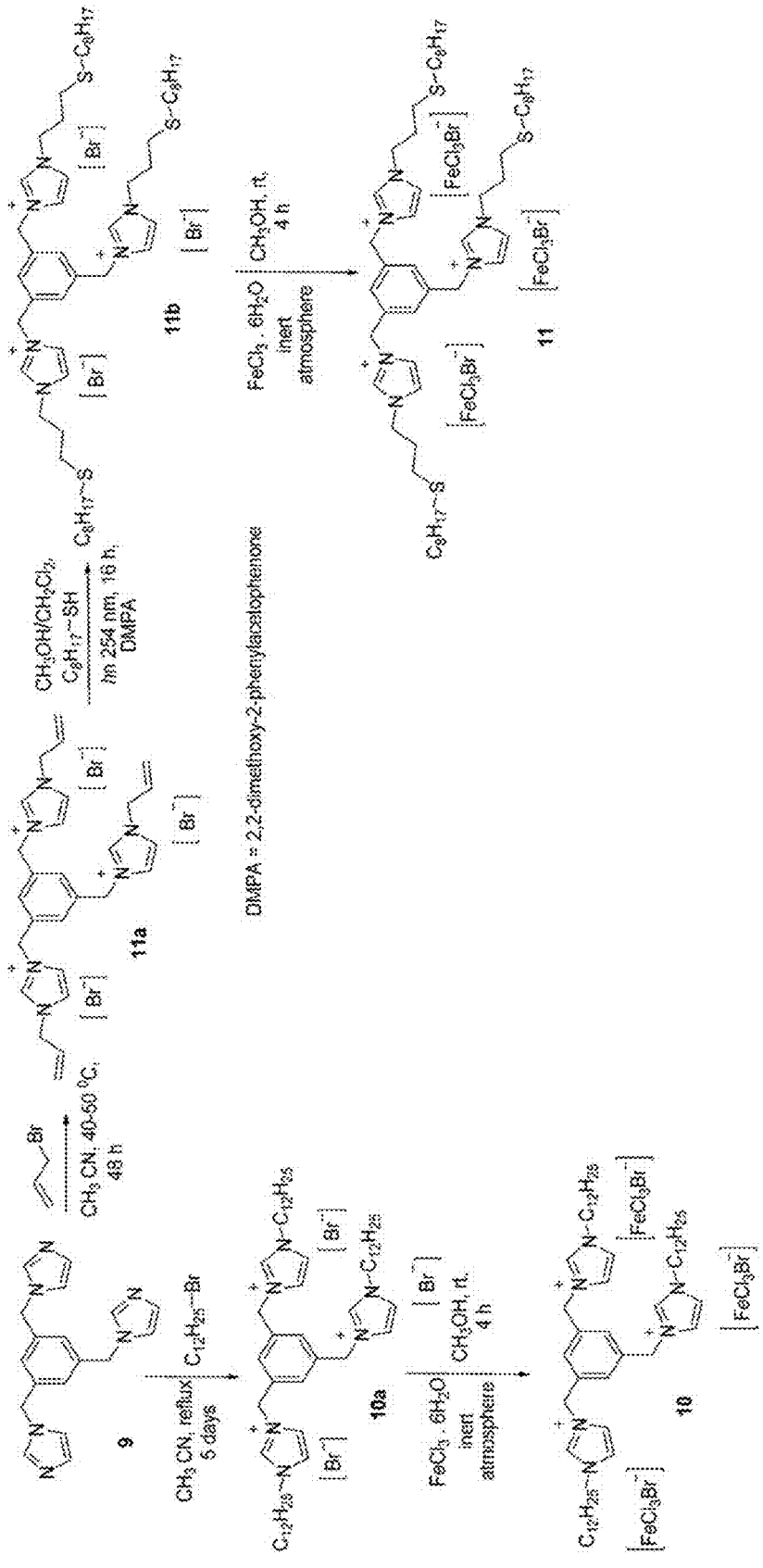
FIG. 4: Scheme 3, showing synthesis of symmetrical tricationic alkylated and thiaalkylated-based hydrophobic magnetic ionic liquids (MILs).

As shown in FIG. 4—Scheme 3, compound 10a was synthesized from compound 9. Compound 10 was prepared by mixing compound 10a (1 mmol) with $FeCl_3·6H_2O$ (3.1 mmol) in methanol under nitrogen atmosphere at room temperature for 4 h. After evaporation of solvent, compound 10 was washed with water (4×10 mL) and dried under vacuum at 60° C. for 12 h.

Characterization of 10a

Yield 87%. $^1$H NMR (400 MHz; CDCl$_3$; ppm): δ0.88 (t, JH—H=6.59 Hz, 9H); 1.26 (m, 54H); 1.89 (m, 6H); 4.22 (t, JH—H=7.32 Hz, 6H); 5.55 (s, 6H); 7.08 (s, 3H); 8.62 (m, 6H); 10.41 (s, 3H). $^{13}$C NMR (400 MHz; CDCl$_3$; ppm): δ14.36; 22.91; 26.51; 29.19; 29.55; 29.59; 29.81; 32.12; 50.45; 52.21; 121.46; 124.62; 132.12; 135.77; 136.58.

Characterization of MIL 10

Yield 94%. A dark brown viscous liquid. The [$FeCl_3Br$—] anion was characterized using visible spectroscopy showing characteristic bands at 534, 619, and 688 nm. Elem. Anal. Calcd (%) for $C_{54}H_{90}Br_3Cl_9Fe_3N_6$ (1549.66): C, 41.85; H, 5.85; N, 5.42. Found: C, 41.65; H, 6.22; N, 5.82.

Synthesis of MIL 11

For the synthesis of MIL 11, shown in FIG. 4—Scheme 3, allyl bromide (0.590 g, 4.89 mmol) was added to a stirred solution of compound 9 (0.50 g, 1.6 mmol) in acetonitrile (15 mL) at 40-50° C. and stirred for 48 h. After evaporating the solvent in vacuo, the residue was washed with hexanes (3×15 mL) and dried under vacuum at 60° C. for 6 h to yield compound 11a. A mixture of 11a (0.30 g, 0.44 mmol), 1-octanethiol (0.579 g, 3.96 mmol), and 2,2-dimethoxy-2-phenylacetophenone (0.169 g, 0.659 mmol) in 10 mL of methanol/dichloromethane (1:1) was then transferred to a quartz tube and stirred until homogeneity. The contents were then exposed to UV radiation (254 nm) for 16 h. The solvent was evaporated and the crude compound washed with hexanes (4×30 mL) under sonication. Removal of residual solvents under vacuum yielded compound 11b. Finally, 11b (1 mmol) was mixed with $FeCl_3·6H_2O$ (3.10 mmol) in methanol at room temperature under nitrogen atmosphere for 4 h to form compound 11. Methanol was evaporated, and MIL 11 was washed with deionized water and dried at 70° C. for 12 h.

Characterization of 11a

Yield 91%; $^1$H NMR (400 MHz; CDCl$_3$; ppm): δ4.89 (d, JH—H=6.59 Hz, 6H); 5.45 (m, 3H); 5.48 (d, JH—H=4.76 Hz, 3H); 5.58 (s, 6H); 5.99 (m, 3H); 7.16 (s, 3H); 8.46 (s, 3H); 8.52 (s, 3H); 10.34 (s, 3H). $^{13}$C NMR (400 MHz; CDCl$_3$; ppm): δ52.28; 52.50; 121.42; 123.23; 124.58; 129.68; 131.91; 135.71; 136.74.

Characterization of 11b

Yield 85%. $^1$H NMR (400 MHz; CDCl$_3$; ppm): δ0.88 (t, JH—H=6.23 Hz, 9H); 1.27 (m, 35H); 1.55 (m, 6H); 2.21 (m, 6H); 2.49 (t, JH—H=7.32 Hz, 6H); 2.55 (t, JH—H=6.59 Hz, 6H); 4.39 (t, JH—H=6.96 Hz, 6H); 5.56 (s, 6H); 7.17 (s, 3H); 8.58 (m, 6H); 10.42 (s, 3H). $^{13}$C NMR (400 MHz; CDCl$_3$; ppm): δ14.67; 23.20; 28.82; 29.43; 29.74; 30.03; 32.35; 32.71; 49.18; 52.66; 122.25; 124.88; 132.53; 136.02; 137.15.

Characterization of MIL 11

Yield 91%. A dark brown viscous liquid. Characteristic bands for the [$FeCl_3Br$—] anion were observed at 534, 619, and 688 nm using visible spectroscopy. Elem. Anal. Calcd (%) for $C_{51}H_{87}Br_3Cl_9Fe_3N_6S_3$ (1606.8): C, 38.12; H, 5.46; N, 5.23. Found: C, 39.10; H, 5.62; N, 5.44.

Synthesis of MIL 12

Figure 5:
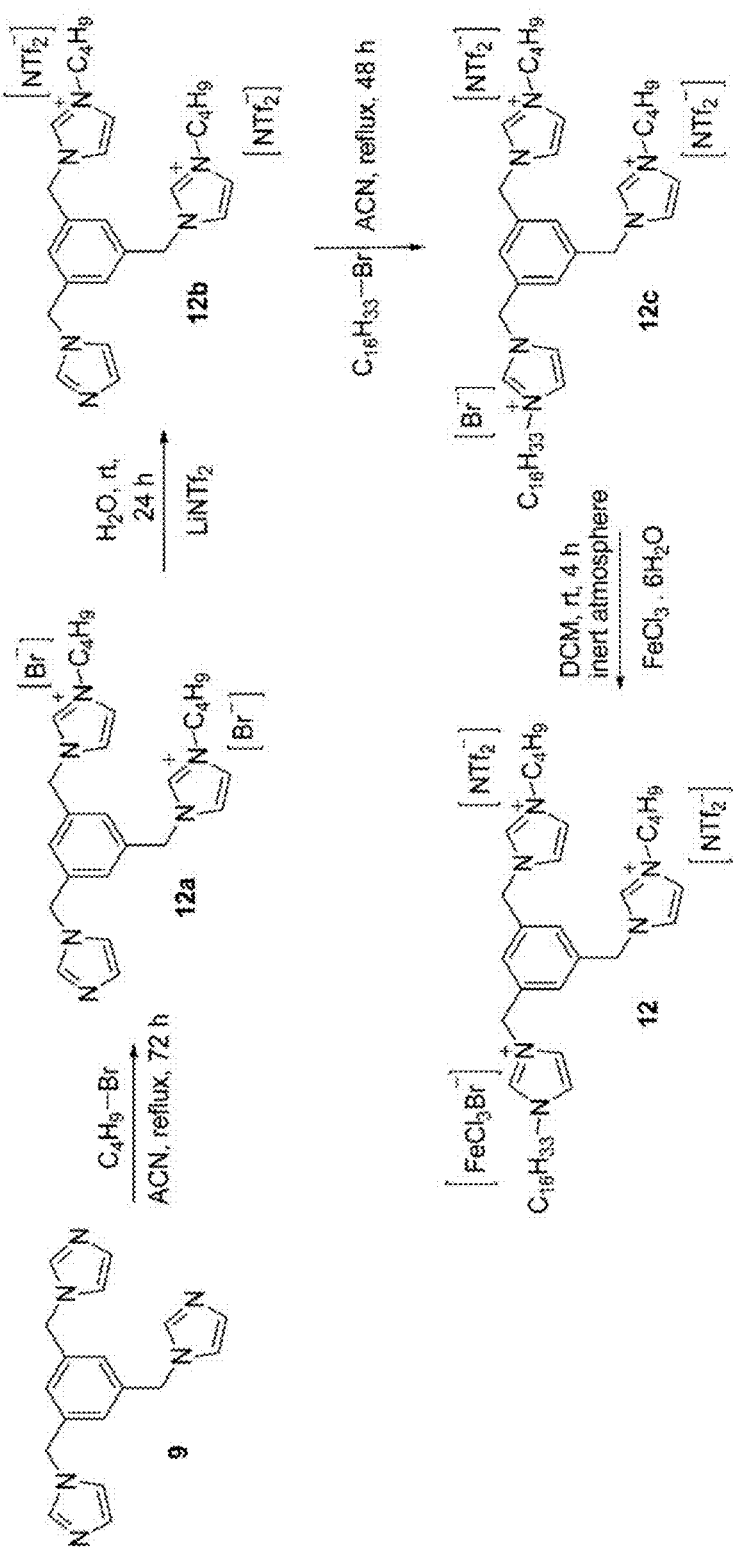
FIG. 5: Scheme 4, showing synthesis of unsymmetrical tricationic heterocation-based hydrophobic magnetic ionic liquids (MILs).

The synthesis of MIL 12 is shown in FIG. 5—Scheme 4. Compound 9 (0.60 g, 1.9 mmol) was dissolved in acetonitrile (50 mL) and added dropwise to a solution of bromobutane (0.517 g, 3.78 mmol) in acetonitrile (20 mL). The reaction mixture was stirred under reflux for 72 h. After evaporation of solvent, the crude compound was washed with diethyl ether (3×30 mL) under sonication for 30 min. Compound 12a (1 mmol) was then dissolved in water and allowed to react with LiNTf2 (2.20 mmol) at room temperature for 24 h. Compound 12b was then filtered and washed several times with water and monitored for the presence of halide impurities by adding silver nitrate. Compound 12b (0.4 g, 0.4 mmol) was reacted with bromohexadecane (0.126 g, 0.413 mmol) in acetonitrile under reflux for 48 h to obtain 12c. After solvent evaporation in vacuo, the residue was washed several times with hexanes (4×10 mL) and dried at 70° C. for 12 h. Finally, MIL 12 was synthesized by reacting 12c (0.30 g, 0.23 mmol) with $FeCl_3.6H_2O$ (0.062 g, 0.25 mmol) in dichloromethane at room temperature for 4 h under nitrogen atmosphere. The solvent was evaporated and MIL 12 was washed with water (10 mL) under sonication to remove unreacted iron chloride.

Characterization of 12a

Yield 78%. $^1$H NMR (400 MHz; DMSO; ppm): δ0.91 (t, JH—H=6.59 Hz, 6H); 1.26 (m, 4H); 1.79 (m, 4H); 4.20 (m, 4H); 5.20 (m, 2H); 5.44 (m, 4H); 6.92 (s, 1H); 7.32 (m, 3H); 7.75 (m, 6H); 9.42 (m, 2H). $^{13}$C NMR (400 MHz; DMSO; ppm): δ14.01; 19.51; 31.96; 49.41; 52.09; 123.27; 123.51; 128.35; 129.36; 136.80; 136.93; 139.77; 140.08.

Characterization of 12b

Yield 91%. $^1$H NMR (400 MHz; DMSO; ppm): δ0.91 (t, JH—H=6.59 Hz, 6H); 1.23 (m, 4H); 1.77 (m, 4H); 4.17 (m, 4H); 5.22 (m, 2H); 5.41 (m, 4H); 7.00 (s, 1H); 7.25 (m, 3H); 7.42 (m, 1H); 7.84 (m, 5H); 9.25 (s, 2H). $^{13}$C NMR (400 MHz; DMSO; ppm): δ13.35; 18.87; 31.35; 48.79; 49.50; 51.51; 122.60; 122.65; 122.92; 126.65; 127.65; 136.18; 136.26;

Characterization of 12c

Yield 85%. $^1$H NMR (400 MHz; DMSO; ppm): δ0.91 (t, JH—H=6.59 Hz, 9H); 1.23 (m, 28H); 1.78 (m, 6H); 4.18 (t, JH—H=7.32 Hz, 6H); 5.43 (s, 6H); 7.46 (s, 3H); 7.76 (s, 3H); 7.85 (s, 3H); 9.33 (s, 3H). $^{13}$C NMR (400 MHz; DMSO; ppm): δ13.34; 18.86; 22.14; 29.09; 31.33; 48.78; 51.41; 122.58; 122.82; 128.66; 136.26.

Characterization of MIL 12

Yield 90%. A dark brown viscous liquid. The [$FeCl_3Br$—] anion was characterized using visible spectroscopy showing absorption bands at 534, 619, and 688 nm. Elem. Anal. Calcd (%) for $C_{46}H_{69}BrCl_3F_{12}FeN_8O_8S_4$ (1460.43): C, 37.83; H, 4.76; N, 7.67. Found: C, 37.33; H, 4.37; N, 7.39.

Preparation of Monocationic Ammonium-Based Hydrophobic MILs

Monocationic MILs that lack acidic protons and are functionalized were developed.

To improve the hydrophobic character of the resulting MIL, trioctylamine was used and quaternized with alkyl halides. The reaction of trioctylamine and butyl/decyl bromide resulted in low yields of the bromide salt (<20%) with most of the starting materials left unreacted, even after 7 days (based on 1H NMR spectroscopy). In contrast, the same reaction conditions with benzyl bromide produced higher yields (>90%) and proceeded to completion within 72 h, as shown in FIG. 2—Scheme 1. While not wishing to be bound by theory, it is now believed herein that this is due to resonance stabilization of the carbocation by the aromatic moiety. However, functionalized benzyl substituents including 3-methoxybenzyl and 4-tert-butylbenzyl can be incorporated into the quaternary ammonium structure, which now allows for unique substitutions within the monocationic MIL framework.

The solubility of the ammonium-based MILs in water and hexane is shown in Table 1. Independent of the substituent functional groups imparted by the quaternization reaction, MILs 1-3 were immiscible with water at compositions as low as 0.1% (w/v) MIL. The hydrophobic properties of the monocationic MILs are thus useful for applications such as aqueous liquid-liquid microextractions, where extremely low phase ratios of extraction solvent are employed.

TABLE 1

Physicochemical and Magnetic Properties of Hydrophobic MILs Synthesized

| MIL | MW (g/mol) | melting point (° C.)[a] | μeff[b] (μB) | thermal stability[c] (° C.) | solubility in hexanes | solubility in water |
|---|---|---|---|---|---|---|
| 1 | 686.9 | −53.2 (Tg) | 5.26 | 258 | I | I[d] |
| 2 | 716.9 | <−65 | 5.60 | 203 | I | I[d] |
| 3 | 743.01 | −50.7 (Tg) | 5.68 | 222 | I | I[d] |
| 4a | 1035.0 | −32.6 (Tg) | 5.40 | 310 | I | I[e] |
| 4b | 1303.6 | <25 | 5.37 | 294 | I | I[e] |
| 6c | 1338.9 | <25 | 7.58 | 299 | I | I[e] |
| 6 | 1375.7 | −0.6 | 5.69 | 314 | I | Id |
| 7 | 1107.1 | −6.7 (Tg) | 5.45 | 311 | I | I[d] |
| 8 | 1191.3 | −16.7 | 5.30 | 312 | I | I[d] |
| 10 | 1549.6 | <−65 | 11.25 | 312 | I | I[e] |
| 11 | 1606.8 | <−65 | 11.76 | 225 | I | I[e] |
| 12 | 1460.4 | 5.0 | 5.10 | 276 | I | I[d] |

[a]-Tg = glass transition temperature.
[b]- μeff = effective magnetic moment measured at 295 K.
[c]-Thermal gravimetric analysis (TGA) = temperature at which 5 wt % loss of MIL is observed;
I = insoluble.
[d]-Insoluble at 0.1% (w/v).
[e]-Insoluble at 0.25% (w/v).

Structural Tuning of Symmetrical/Unsymmetrical Dicationic Hydrophobic MILs

Dicationic ILs provide more opportunities for control of physical and chemical properties, as compared to conventional monocationic ILs. The dicationic IL platform is especially useful for MILs, which require at least a paramagnetic anion to provide sufficient magnetic susceptibility.

One cation in a dicationic system was paired with the [NTf2-] anion and produced functionalized hydrophobic MILs based on imidazolium cations. In general, the synthesis of symmetrical imidazolium-based dicationic MILs was performed in three steps. First, a dicationic bromide salt was synthesized with alkyl/aromatic substituents on the cation. A dodecyl linkage chain between the imidazolium-based cations was employed to increase the conformational degrees of freedom, thus improving the likelihood of forming low-melting MILs. Two homoanion precursors were then synthesized from the dibromide salt, either by anion exchange to incorporate hydrophobic [NTf2-] anions or reaction with $FeCl_3.6H_2O$ to generate paramagnetic [$FeCl_3Br$—] anions. Finally, mixing equimolar quantities of the [NTf2-] and [$FeCl_3Br$—] salts produced dicationic MILs with heteroanions.

When functionalized with benzyl substituents, the imidazolium-based dicationic MIL 4a exhibited water solubility below 0.25% (w/v), as shown in Table 1. Blocking the acidic C-2 proton of the hexadecyl functionalized imidazolium dication with a methyl group (4b) resulted in similar water solubility to 4a. The hydrophobicity of this class of MILs was significantly improved by replacing the imidazolium cation with the benzimidazolium cation.

MILs 6 and 7 were synthesized according to FIG. 1—Scheme 1. Improved hydrophobic character was observed for 6 and 7, which were insoluble in water at 0.1% (w/v) MIL.

Another structural feature that affects the physicochemical properties of ILs is the presence of asymmetry in the molecule. Dicationic ILs are uniquely amenable to unsymmetrical archetypes since it is possible to independently functionalize the cationic moieties. Since there was improved hydrophobicity obtained for dicationic MILs 6 and 7, a MIL that tethers benzimidazolium and imidazolium cations was produced. FIG. 3—Scheme 2 illustrates the synthesis of the heterocationic MIL 8. Initially, reaction of 1,12-dibromododecane with benzylimidazole in a 1:1 mole ratio resulted in formation of 20% (based on $^1$H NMR) of the dibromide salt. However, increasing the mole ratio of 1,12-dibromododecane to 4.5:1 significantly reduced the formation of the dibromide salt to ≤5%, based on $^1$H NMR. The metathesis reaction of compound 8a with 1.2 mol equiv of LiNTf2 formed a precipitate (8b) while the dicationic [Br—]/[NTf2-] analogue remained in the aqueous phase. After the incorporation of the hydrophobic anion, compound 8b was reacted with previously synthesized hexadecylbenzimidazole to generate the unsymmetrical dicationic [Br—]/[NTf2-] salt 8c. Finally, hydrophobic MIL 8 was synthesized by reacting compound 8c with $FeCl_3.6H_2O$. Similar to MILs 1-3, 6, and 7, the heterocationic MIL 8 was insoluble in water down to 0.1% (w/v) MIL.

Synthesis of Symmetrical Alkylated/Thiaalkylated and Unsymmetrical Tricationic Hydrophobic MILs The synthesis of symmetrical tricationic hydrophobic MILs 10 and 11 is shown in FIG. 4—Scheme 3. With the aim of minimizing water solubility of the resulting MILs, a relatively hydrophobic benzene core functionalized with three imidazole moieties was selected as a precursor and prepared accordingly. Compound 9 was then alkylated by reaction with 1-bromododecane for 5 days in acetonitrile to generate compound 10a. Subsequent mixing with $FeCl_3.6H_2O$ produced hydrophobic MIL 10. From FIG. 4—Scheme 3, it is now shown that synthesis of the tribromide salt 10a was the most time-consuming step. In an effort to reduce the time required for the generation of a MIL with similar magnetic susceptibility and hydrophobicity to MIL 10, thiolene click chemistry was employed.

The tricationic hydrophobic MIL 11 was synthesized as shown in FIG. 4—Scheme 3. For synthesis of MIL 11, intermediate 9 was reacted with allyl bromide for 48 h in acetonitrile to produce compound 11a. In comparison to the sluggish formation of the bromide salt 10a, compound 11a was more rapidly generated, due to the resonance stabilization of allylic carbocation. Compound 11b was prepared by reacting 11a with octanethiol in a methanol/dichloromethane (1:1) solvent mixture in the presence of UV irradiation for 16 h. Exclusive formation of anti-Markovnikov-oriented products was confirmed by $^1$H NMR. Excess amounts of unreacted starting materials were removed by washing the crude compound with hexanes. Thus, the total reaction time required for the generation of the thiaalkyl-based tribromide salt (11b) was significantly less in comparison with 10a. Finally, the hydrophobic MIL 11 was prepared by reacting 11b with $FeCl_3.6H_2O$. Table 1 shows that MILs 10 and 11 are insoluble in aqueous solution down to 0.25% (w/v) MIL.

In order to improve the hydrophobic character of the tricationic MILs, hydrophobic [NTf2] anions were incorporated into the molecular structure, as shown in MIL 12. When intermediate 9 is reacted with alkyl halides such as 1-bromooctane, subsequent anion exchange with [NTf2] leads to the formation of room-temperature solids (Tm=51.1° C.). Formation of MILs with lower melting points involved reacting intermediate 9 with 1-bromobutane to yield the dibromide salt (12a), as shown in FIG. 5—Scheme 4. Hydrophobic [NTf2-] anions were then incorporated by metathesis reaction of 12a. Generation of the unsymmetrical tricationic IL was accomplished by reacting 12b with 1-bromohexadecane to produce compound 12c. Finally, MIL 12 was generated by reacting compound 12c with $FeCl_3.6H_2O$ in dichloromethane for 4 h. As shown in Table 1, MIL 12 exhibited improved hydrophobicity in comparison to MILs 10 and 11.

Thermal Properties of Hydrophobic MILs

The phase transition behavior and thermal stability of the hydrophobic MILs were examined using DSC and TGA, and the results compiled in Table 1. Monocationic MILs 1 and 3 exhibited glass transition temperatures (Tg) of −53.2 and −50.7° C., respectively. A melting point (Tm) for MIL 2 could not be detected above −65° C. These values were much lower in comparison with ammonium-based MILs possessing only linear alkyl substituents. The total number of carbon atoms and asymmetry of the cation structure govern the Tm of quaternary ammonium salts. Hence, the relatively low Tg of MILs 1 and 3 may be explained by the asymmetry resulting from incorporation of aromatic moieties within the cation structure. Interestingly, while MIL 1 was thermally stable up to 258° C., similar weight loss (5%) was observed at lower temperatures for the methoxy (2) and tert-butyl (3) functionalized monocationic MILs.

Symmetrical dicationic MILs with heteroanions (4a, 4b, 6, and 7) exhibited higher phase transition temperatures than the monocationic MILs but were nonetheless liquids at room temperature. Despite similar cation substituents, MIL 7 exhibited a higher Tg than 4a which may be attributed to enhanced π-π interactions as a consequence of the benzimidazolium cation. The dicationic MILs exhibited no more than 5% weight loss below temperatures ranging from 294 to 312° C. No significant enhancement in thermal stability was observed for the dicationic MILs containing [NTf2-]/[FeCl$_3$Br—] heteroanions compared to those containing 2[FeCl$_3$Br—] homoanions.

The effect of dissimilar cationic moieties on the melting point of dicationic MILs is shown in FIG. 1B. Unsymmetrical replacement of the hexadecylbenzimidazolium cation with the benzylimidazolium cation lowered the Tm from −0.6 to −16.7° C. (MILs 6 and 8, respectively), an outcome that is attributed to diminished π-π0 interactions as well as removal of the dication symmetry component. Analogous to conventional dicationic ILs, endothermic peaks in DSC traces were quite broad with observable shouldering. This is now believed herein to be due to the highly flexible nature of the MIL cations, which allows different conformations and multiple step phase transitions.

Phase transitions were not observed above −65° C. for the heavily alkylated/thiaalkylated symmetrical tricationic MILs 10 and 11. Both compounds 10 and 11 are room temperature liquids in contrast to their corresponding bromide salts. This is a function of incorporating the weaker coordinating [FeCl$_3$Br—] anion. The thermal decomposition temperatures varied significantly between the alkylated (10) and thiaalkylated (11) hydrophobic tricationic MILs. Possessing a more thermally labile C—S bond, MIL 11 exhibited 5% weight loss at 225° C. compared to 312 and 275° C. for MIL 10 and 12, respectively.

Magnetic Properties of Hydrophobic MILs

The paramagnetic properties of MILs provide a unique advantage over conventional ILs by permitting control over substrate motion through the application of an external magnetic field. MILs containing high-spin d5 iron(III) centers are well characterized owing to the abundance and low cost of iron materials and exhibit paramagnetism at ambient temperatures. Table 1 shows the effective magnetic moments for all MILs, determined using an Evans magnetic susceptibility balance. The general expression for molar magnetic susceptibility using the Evans balance is shown in eq 1:

$$X_M = \frac{C_{bal}LM(R - R_o)}{10^9 m} \quad (1)$$

where XM represents the molar magnetic susceptibility, $C_{bal}$ is the balance calibration constant, L corresponds to the length of the sample in the tube, M is the molecular weight of the compound being measured, R is the instrument reading for the sample in the tube, $R_o$ is the instrument reading for the empty sample tube, and m is the mass of sample introduced into the Evan's balance. From XM, it is possible to calculate μeff according to eq 2:

$$\mu_{eff} = 2.83\sqrt{X_M T} \quad (2)$$

where T is the absolute temperature. The μeff for ammonium-based monocationic MILs ranged from 5.26 to 5.68 μBand were comparable to those determined for heteroanionic MILs possessing a single [FeCl$_3$Br—] anion (4a, 4b, 6, 7, 8, and 12). In order to increase the magnetic susceptibility of MILs, multiple paramagnetic iron(III) centers were incorporated into the MIL structure. For example, dicationic MIL 6c was designed to possess two paramagnetic iron(III) centers providing an increase in μeff to nearly 7.6 μB. Further enhancement of magnetic susceptibility was observed in tricationic MILs 10 and 11, which exhibited μeff=11.25 μB and 11.76 μB, respectively. The iron(III)-based MILs represent an inexpensive and useful alternative to MILs based on lanthanides, such as Dy(III) (μeff=10.6 μB). Moreover, the higher response of MILs 10 and 11 toward magnetic fields enables the use of smaller magnets with lower field strength for their manipulation in solution, which is useful in miniaturized magnet-based systems.

Discussion of Example 1

In Example 1, three general classes of hydrophobic MILs were successfully synthesized and characterized. Within each class, the synthetic approaches now described herein were used to control the magnetic and physicochemical properties of MILs. The incorporation of benzyl substituents within the MIL structure of monocationic quaternary ammonium-based hydrophobic MILs produced lower melting point compounds compared to linear alkyl substituents. The hydrophobicity of dicationic MILs was enhanced by replacing imidazolium cations with benzimidazolium cations, resulting in MILs that are insoluble in water down to 0.1% (w/v). Moreover, the inclusion of asymmetry within the cationic portion of dicationic MILs lowered the melting point without sacrificing hydrophobicity or magnetic susceptibility. Additionally, increasing the number of paramagnetic iron(III) centers in the MIL structure resulted in higher μeff values. Throughout the preparation of tricationic MILs, a common intermediate was chosen and modified to alter the hydrophobicity and magnetic properties of resulting MILs. Tricationic MILs containing three [FeCl$_3$Br—] anions exhibited μeff values as high as 11.76 μB, representing the highest known value reported for MILs. The synthesis of iron(III)-based tricationic hydrophobic MILs possessing large μeff is an inexpensive alternative to MILs based on lanthanides.

Example 2

Extraction of DNA by Magnetic Ionic Liquids: Tunable Solvents for Rapid and Selective DNA Analysis Several hydrophobic MILs, namely 1,12-bis[N—(N'-hexadecylbenzimidazolium) dodecane bis[(trifluoromethyl-isulfonyl]imide bromotrichloferrate(III) [(C$_{16}$BnIM)$_2$C$_{12}$$^{2+}$][NTf2-, FeCl$_3$Br—]) (13); benzyltrioctylammonium bromotrichloferrate(III) ([(C$_8$)$_3$BnN$^+$][FeCl$_3$Br—]) (14); and, trihexyl(tetradecyl)phosphonium tetrachloferrate(III) ([P$_{6,6,6,14+}$][FeCl$_4$—]) (15), were used for the direct extraction of DNA from an aqueous solution. Isolation of the extraction phase was achieved by applying an external magnetic field, thereby circumventing time-consuming centrifugation steps. The optimized MIL-based extraction procedures are capable of performing rapid and highly efficient extraction of double-stranded and single-stranded DNA from a matrix containing metal ions and protein. Plasmid DNA (pDNA) extracted from a bacterial cell lysate using the MIL-based method is now shown to be a high quality template for PCR.

Reagents

Benzimidazole, trioctylamine, 1,12-dibromododecane, and guanidine hydrochloride (GuHCl) were purchased from Acros Organics (NJ, USA). Trihexyl(tetradecyl)phosphonium chloride was purchased from Strem Chemicals (Newburyport, Mass., USA). Deuterated chloroform was obtained through Cambridge Isotope Laboratories (Andover, Mass. USA). Iron(III) chloride hexahydrate (FeCl$_3$.6H$_2$O), 1-bromohexadecane, benzyl bromide, sodium dodecyl sulfate (SDS), albumin from chicken egg white, and DNA sodium salt from salmon testes (stDNA, approximately 20 kbp) were purchased from Sigma-Aldrich (St. Louis, Mo., USA). Sodium chloride, sodium hydroxide, potassium chloride, calcium chloride dihydrate, magnesium chloride hexahydrate, potassium acetate, silica gel sorbent (230-400 mesh), and tris(hydroxymethyl)aminomethane hydrochloride (Tris-HCl) were purchased from Fisher Scientific (Fair Lawn, N.J., USA). Synthetic oligonucleotides including duplex (20 bp, molecular weight=12 232 Da), single-stranded DNA oligonucleotides (33 mer, molecular weight=10 075 Da), and primers were purchased from IDT (Coralville, Iowa, USA). The pET-32 plasmid was obtained from EMD Millipore (Billerica, Mass., USA). NEB 5-alpha Competent Escherichia coli cells and Phusion High-Fidelity DNA Polymerase were obtained from New England Biolabs (Ipswich, Mass., USA). Agarose and tris(hydroxymethyl)aminomethane (Tris) were obtained from P212121 (Ypsilanti, Mich., USA). A 1 Kb Plus DNA Ladder (250-25,000 bp) was obtained from Gold Biotechnology, Inc. (St. Louis, Mo., USA) with SYBR Safe DNA gel stain and bromophenol blue being supplied by Life Technologies (Carlsbad, Calif., USA) and Santa Cruz Biotech (Dallas, Tex., USA), respectively. QIAquick Gel Extraction and QIAamp DNA Mini Kits were purchased from QIAgen (Valencia, Calif., USA). Deionized water (18.2 MΩ cm) obtained from a Milli-Q water purification system was used for the preparation of all solutions (Millipore, Bedford, Mass., USA).

Synthesis and Characterization of Hydrophobic Magnetic Ionic Liquids

The synthesis of two hydrophobic MILs, namely, [(C$_{16}$BnIM)$_2$C$_{12}$$^{2+}$][NTf2-, FeCl$_3$Br—] (13) and [(C$_8$)$_3$BnN+][FeCl$_3$Br—] (14), was carried out as described herein. $^1$H NMR, $^{13}$C NMR, ESI-MS, and UV-vis were used to characterize the three MILs.

Instrumentation

High performance liquid chromatography with UV detection was performed on a LC-20A liquid chromatograph (Shimadzu, Japan) consisting of two LC-20AT pumps, a SPD-20 UV/vis detector, and a DGU-20A3 degasser. Chromatographic separations were performed on a 35 mm×4.6 mm i.d.×2.5 μm TSKgel DEAE-NPR anion exchange column with a 5 mm×4.6 mm i.d.×5 μm TSKgel DEAE-NPR guard column from Tosoh Bioscience (King of Prussia, Pa.). The column was equilibrated with a mobile phase composition of 50:50 (A) 20 mM Tris-HCl (pH 8), and (B) 1 M NaCl/20 mM Tris-HCl (pH 8). For stDNA analysis, gradient elution was performed beginning with 50% mobile phase B and increased to 100% B over 10 min. In the separation of ssDNA as well as DNA and albumin, the column was first equilibrated with 20 mM Tris-HCl followed by gradient elution from 0% to 50% B over 10 mM and then 50% to 100% B over 5 mM. A flow rate of 1 mL min-1 was used for all HPLC separations. DNA and albumin were detected at 260 and 280 nm, respectively.

All extractions were performed in 4 mL screw cap vials. Isolation of the magnetic ionic liquid extraction phase was achieved using a cylinder magnet (B=0.9 T) or rod magnet (B=0.66 T) obtained from K&J Magnetics (Pipersville, Pa.). A Techne FTgene2D thermal cycler (Burlington, N.J., USA) was used for all PCR experiments. Agarose gel electrophoresis was performed in a Neo/Sci (Rochester, N.Y.) electrophoresis chamber with a dual output power supply. Gels were visualized at 468 nm on a Pearl Blue Transilluminator (Pearl Biotech, San Francisco, Calif.).

MIL-Based Single Droplet Extraction

The MIL-based static single droplet extraction (SDE) method was performed. Briefly, a 20 μL droplet of MIL was suspended from a magnetic rod (B=0.66 T) and lowered into a 4.17 nM solution of stDNA buffered by 20 mM Tris-HCl (pH 8). After 5-120 min, the MIL droplet was removed from the sample and a portion of the aqueous phase subjected to HPLC analysis to determine the concentration of DNA remaining after extraction.

MIL-Based Dispersive Droplet Extraction

The general MIL-based dispersive droplet extraction (DDE) approach was used. Briefly, a 4.17 nM solution of stDNA was prepared in 20 mM Tris-HCl (pH 8). An optimized volume of MIL (typically 20 μL) was added to the aqueous DNA solution and manually shaken for 5-60 s, resulting in a dispersion of the hydrophobic MIL in the aqueous phase. In the case of the $[(C_{16}BnIM)_2C_{12}^{2+}][NTf2-, FeCl_3Br—]$ MIL, it was gently heated prior to extraction. The vial was then placed in a 0.9 T magnetic field to facilitate the rapid isolation of MIL followed by HPLC analysis of a 20 μL aliquot of the aqueous phase.

Extraction of Synthetic Oligonucleotides and Duplex DNA

Solutions of synthetic oligonucleotides and duplex DNA were prepared such that the mass of DNA in aqueous solution was consistent with the experiments involving stDNA (100 μg of stDNA in 2 mL of Tris-HCl). For extractions of ssDNA, a 33 base oligonucleotide with sequence 5'-CAC CAT GAC AGT GGT CCC GGA GAA TTT CGT CCC-3' [SEQ ID NO:1] was dissolved in 20 mM Tris-HCl (pH 8) resulting in a final concentration of 1499 nM. In the case of synthetic dsDNA, an aqueous solution containing 1224 nM of 20 bp duplex (sequence: 5'-ATG CCT ACA GTT ACT GAC TT-3' [SEQ ID NO:2] and its complementary strand) was prepared in 20 mM Tris-HCl (pH 8). Solutions containing single-stranded oligonucleotides or duplex DNA were subjected to MIL-based DDE with a 20 μL portion of the aqueous phase being analyzed by HPLC.

Extraction of DNA from a Complex Matrix

Sample matrices containing either metal ions or protein (albumin) were prepared from stock solutions. A sample solution containing 388 mM NaCl, 153 mM KCl, 38.1 mM $CaCl_2.2H_2O$, 28.3 mM $MgCl_2.6H_2O$, and 4.17 nM stDNA was extracted in triplicate using MIL-based DDE for all three MILs. For experiments involving protein as a matrix component, the samples were prepared at an albumin concentration of 3.4 μM and stDNA concentration of 4.17 nM with the pH varied from 3.5 to 8.

PCR and DNA Sequence Analysis

For DNA sequence analysis, a modified pET-32 plasmid containing an 879 bp gene encoding human 5'-methylthio-adenosine phosphorylase (MTAP) was extracted using the $[(C_8)_3BnN+][FeCl_3Br—]$ MIL in the DDE approach. The pDNA-enriched MIL microdroplet was removed from solution using a 0.66 T rod magnet and stored at room temperature for 24 h. Recovery of the pDNA was achieved by dispersion of the MIL microdroplet in 200 μL of 20 mM Tris-HCl (pH 8) for 2 min. A 2 μL aliquot of the aqueous phase was subjected to PCR using primers for the MTAP gene. The PCR products were separated by agarose gel electrophoresis, and the band containing the MTAP gene was extracted from the gel using a QIAquick Gel Extraction Kit. An external DNA sequencing service (Eurofins Genomics, Huntsville, Ala.) performed sequence analysis of the MTAP gene amplified from the pDNA recovered from the MIL extraction phase.

Amplification of the MTAP gene was performed using the primers 5'-TGC TGT TCC AGG GAC CT-3' [SEQ ID NO:3] (molecular weight=5,177.4 Da) and 5'-GAA TTC GGA TCC GGA CGC-3' [SEQ ID NO:4] (molecular weight=5,524.6 Da). A 2 μL aliquot of aqueous solution containing pDNA recovered from the MIL extraction phase was added to a PCR tube with 34.5 μL of DI $H_2O$ and 10 μL of 5× Phusion HF buffer. Primers and dNTPs were added to achieve a final concentration of 0.2 μM and 200 μM, respectively. Finally, 1 unit of Phusion High Fidelity DNA polymerase was added to the reaction mixture. The total reaction volume was 50 μL. The following temperature program was used for amplification of MTAP: 5 mM initial denaturation at 95° C. and 30 cycles comprised of a 30 s denaturation step at 95° C., a 45 s hold at 54° C. for annealing, and a 45 s elongation step at 72° C.

Recovery of DNA from the MIL Extraction Phase

Following MIL-based DDE of a 4.17 nM solution of stDNA, the DNA-enriched MIL microdroplet was first transferred into a microcentrifuge tube containing 1 mL of 3 M potassium acetate (pH 4.8) and vortexed for 2 min, ensuring a homogeneous solution. A silica sorbent column was constructed by measuring 750 mg of silica particles into a Pasteur pipet with the exit end blocked by a glass wool frit. The column was conditioned with 2 mL of 6 M GuHCl, and the sample was subsequently loaded at approximately 1 mL min-1. The sorbent was flushed with 1 mL of isopropanol and the first fraction collected. Next, 750 μL of ethanol was added, and the turbid solution was centrifuged at 16,200 g for 15 mM. The pellet was washed with 80% ethanol for 1 mM. The sample was centrifuged once more at 16,200 g for 10 mM, and the supernatant was decanted. The pellet was dried under an air stream and reconstituted in 100 μL of Tris-HCl (pH 8), and a 20 μL aliquot was removed for HPLC analysis.

As an alternative, a rapid approach to DNA recovery was employed. After MIL-based DDE, the DNA-enriched MIL microdroplet was collected from aqueous solution using a 0.66 T rod magnet and immersed in 200 µL of Tris-HCl (pH 8) for 2 mM. The microdroplet was then removed from solution and the aliquot subjected to PCR amplification.

Extraction of DNA from Bacterial Cell Lysate

The conditions used to culture NEB 5-alpha Competent *E. coli* cells containing pDNA were as follows: NEB 5-alpha Competent *E. coli* cells were transformed with modified pET-32 plasmid DNA (pDNA) containing the 5'-methylthioadenosine phosphorylase (MTAP) gene. A 1 µL aliquot of purified pDNA (347 ng µL-1) was added to a microcentrifuge tube containing 20 µL of competent *E. coli* cells. The mixture was set on ice for 30 mM. The solution was placed in a water bath at 40° C. for 42 s and subsequently chilled on ice for 2 mM. A 250 µL aliquot of Luria Bertani (LB) media was added to the solution, which was then incubated at 37° C. for 1 h. Transformed *E. coli* cells were incubated in 100 mL of LB media with 200 µg mL-1 carbenicillin at 37° C. for 20 h.

A 10 mL aliquot of an overnight *E. coli* cell culture was centrifuged at 16,200 g for 5 min and resuspended in 300 µL of 20 mM Tris buffer containing 10 mM EDTA (pH 8). Lysozyme (200 µg) was added to the solution, which was then incubated for 5 mM at room temperature, followed by the addition of 600 µL of 0.2 N NaOH, 1% SDS (w/v). After gentle mixing of the solution, 400 µL of 3 M potassium acetate (pH 4.8) was added. The contents were thoroughly mixed and centrifuged at 16,200 g for 10 mM. A 400 µL aliquot of the supernatant was transferred to a clean vial, and the solution was extracted using the MIL-based DDE approach. The pDNA was then recovered using either the aforementioned silica-based or the rapid immersion procedure prior to PCR amplification.

Structural Design of Hydrophobic MILs for DNA Extraction

Figure 6:
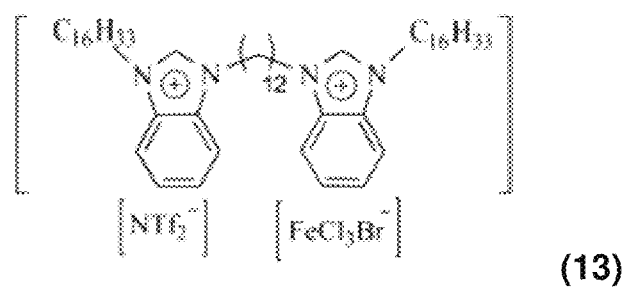
FIG. 6: Structures of three hydrophobic MILs: (13) $[(C_{16}BnIM)_2Cl_{12}^{2+}][NTf2-, FeCl_3Br—]$; (14) $[(C_8)_3BnN+]—[FeCl_3Br—]$, and (15) $[P_{6,6,6,14+}][FeCl_4—]$.
Figure 6:
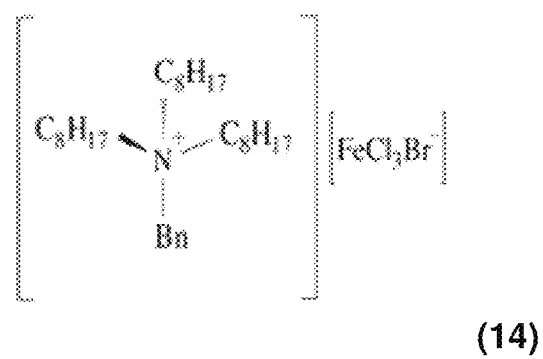
Figure 6:
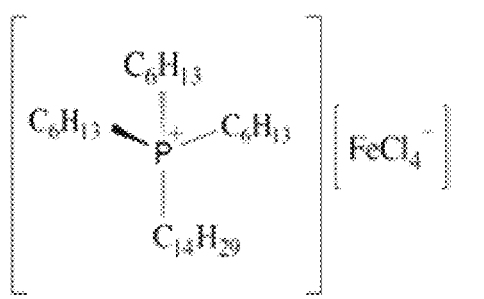

In order to develop sufficiently hydrophobic MILs that still possess paramagnetic behavior, a dicationic platform with [NTf2-]/[FeCl$_3$Br—] heteroanions was chosen. As shown in FIG. 6, the [(C$_{16}$BnIM)$_2$C$_{12}^{2+}$][NTf2-, FeCl$_3$Br—] MIL is comprised of both hydrophobic and paramagnetic anions. Although a greater magnetic moment can be achieved by employing two [FeCl$_3$Br—] anions in a dicationic MIL, increased water-miscibility is also observed. The cationic portions of the [(C$_{16}$BnIM)$_2$C$_{12}^{2+}$][NTf2-, FeCl$_3$Br—] and [(C$_8$)$_3$BnN+][FeCl$_3$Br—] MILs are functionalized with long alkyl chains and benzyl moieties, which significantly increases their overall hydrophobicity.

Optimization of DNA Extraction Mode

The amount of DNA extracted by the hydrophobic MIL extraction phases was evaluated indirectly by subjecting an aliquot of the postextraction aqueous phase to HPLC analysis. An external calibration curve for both dsDNA and ssDNA was established and used to calculate the DNA concentration in aqueous solution. Values of extraction efficiency (E) were obtained using the relationship between the DNA concentration in the aqueous phase following extraction ($C_{aq}$) and the concentration of DNA in the standard solution ($C_{st}$), as shown in eq 3:

$$E = \left[1 - \frac{C_{aq}}{C_{st}}\right] \times 100 \quad (3)$$

Time-consuming centrifugation steps in extraction and purification protocols represent a major bottleneck in nucleic acid sample preparation. In the development of MIL-based DNA extraction methods, considerable attention was given to the compromise between extraction time and efficiency. Identical volumes of MIL were used to extract DNA from an aqueous solution using both SDE and DDE modes. One advantage of DDE over SDE is the dynamic mixing of the MIL extraction solvent with the aqueous medium, which allows for rapid distribution of DNA between the two phases. This is illustrated in Table 2 where the extraction efficiency of stDNA is shown for the [(C$_{16}$BnIM)$_2$C$_{12}^{2+}$][NTf2-, FeCl$_3$Br—] MIL using both SDE and DDE modes. The relatively low extraction efficiencies observed for the SDE technique, particularly at short extraction times, are likely due to less available MIL surface area for interaction with DNA when compared to DDE. The precision of each extraction mode ranged from 1.6 to 8.7% and 0.4 to 3.4% for SDE and DDE, respectively, using triplicate extractions. While the SDE mode required 2 h to achieve an extraction efficiency of 63.1%, the DDE mode provided efficiencies greater than 76% after just 30 s of dynamic mixing and 5 s of phase isolation by exposure to a magnetic field. No appreciable gain in extraction efficiency was observed when the magnetic field was applied at time points greater than 5 s. Therefore, DDE was selected as the optimum extraction mode for subsequent DNA extractions using the three hydrophobic MILs.

TABLE 2

Comparison of Single Droplet and Dispersive Droplet Extraction Modes for the Extraction of stDNA from an Aqueous Solution Using the [(C$_{16}$BnIM)$_2$C$_{12}^{2+}$][NTf2-, FeCl$_3$Br-] MIL Single Droplet Extraction[a]

| time (min) | % extraction efficiency (n = 3) | % RSD |
|---|---|---|
| 10 | 5.5 | 1.6 |
| 20 | 33.3 | 3.0 |
| 30 | 40.5 | 8.7 |
| 60 | 60.3 | 3.3 |
| 90 | 61.6 | 8.6 |
| 120 | 63.1 | 4.1 |

Dispersive Droplet Extraction[b]

| time (s)[c] | % extraction efficiency (n = 3) | % RSD |
|---|---|---|
| 5 | 76.8 | 3.4 |
| 30 | 75.6 | 0.4 |
| 60 | 79.3 | 2.3 |
| 120 | 76.5 | 2.1 |
| 300 | 77.0 | 1.2 |

[a]Conditions: DNA concentration: 4.17 nM; volume of MIL: 20 µL; total solution volume: 2 mL; pH 8.
[b]Conditions: Manual agitation time: 30 s; all other experimental parameters unchanged.
[c]Refers to duration of applied magnetic field.

Effect of MIL Volume on Extraction Efficiency

Figure 7:
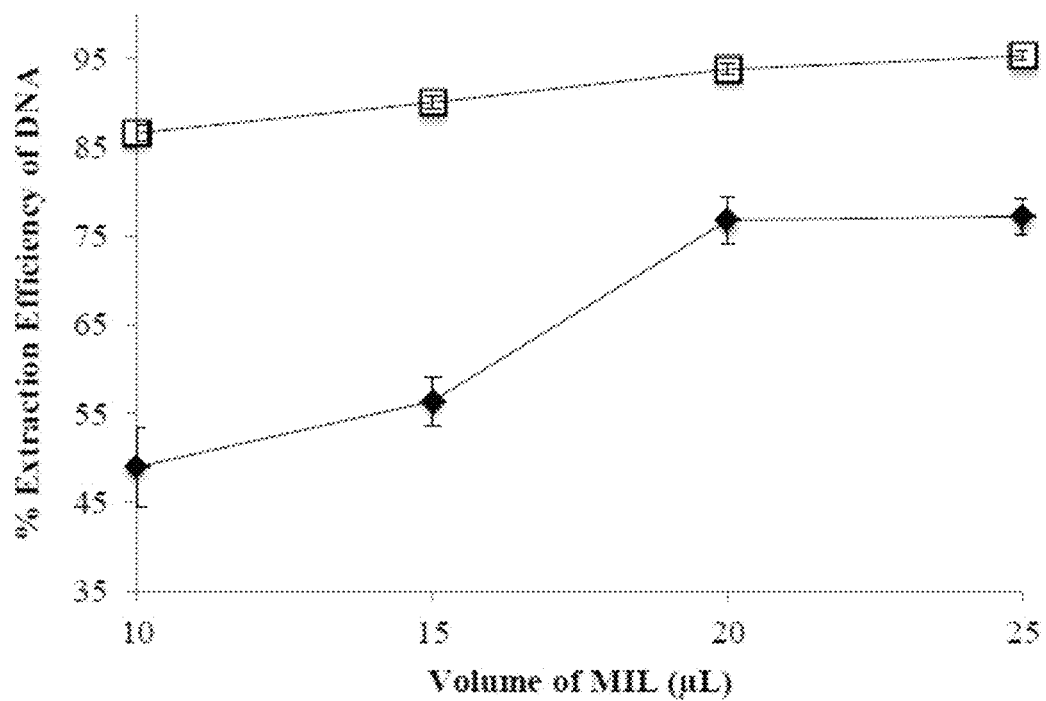
FIG. 7: Effect of MIL volume on extraction efficiency of stDNA. Open squares (□) denote the $[P_{6,6,6,14+}][FeCl_4—]$ MIL, and diamonds (♦) represent the $[(C_{16}BnIM)_2C_{12}^{2+}][NTf2-, FeCl_3Br—]$ MIL.

The effect of MIL volume on extraction efficiency was investigated for the [(C$_{16}$BnIM)$_2$C$_{12}^{2+}$][NTf2-, FeCl$_3$Br—] and [P$_{6,6,6,14+}$][FeCl$_4$—] MILs. A 2 mL solution of 4.17 nM stDNA was extracted using MIL volumes ranging from 10 to 25 µL. As shown in FIG. 7, larger volumes of extraction solvent provided improved DNA extraction efficiencies for both MILs. Higher extraction efficiencies were obtained using the monocationic [P$_{6,6,6,14+}$][FeCl$_4$—] MIL compared to the dicationic [(C$_{16}$BnIM)$_2$C$_{12}^{2+}$][NTf2-, FeCl$_3$Br—]

MIL, even at larger droplet volumes. A significant increase in extraction efficiency was observed for the [(C$_{16}$BnIM)$_2$C$_{12}$$^{2+}$][NTf2-, FeCl$_3$Br—] MIL when the MIL microdroplet volume was increased from 15 to 20 μL, showing a saturation effect at lower volumes of extraction solvent. However, the enhancement of extraction efficiency for the [P$_{6,6,6,14+}$][FeCl$_4$] MIL was much less pronounced. Because 20 and 25 μL showed similar extraction efficiencies, the smaller microdroplet volume was used in subsequent tests. All three MILs examined retained their hydrophobic character and exhibited phase separation when subjected to the external magnetic field, even at very low microdroplet volumes (e.g., 10 μL).

Effect of pH on Extraction Efficiency

The pH of environmental or biological DNA sample solutions is often variable and may have implications on the extraction behavior of interfering matrix components. As pH adjustments are often employed in sample pretreatment steps to minimize the coextraction of contaminants, it is desired to examine its effect on the MIL-based extraction of DNA. To investigate the effect of pH on extraction efficiency, solutions of stDNA ranging from pH 2.5-10.9 were prepared and subjected to MIL-based DDE. The phosphate groups of DNA molecules possess pKa values below the studied pH range. Therefore, they bear negative charges capable of favorable electrostatic interactions with the MIL cation.

Figure 8:
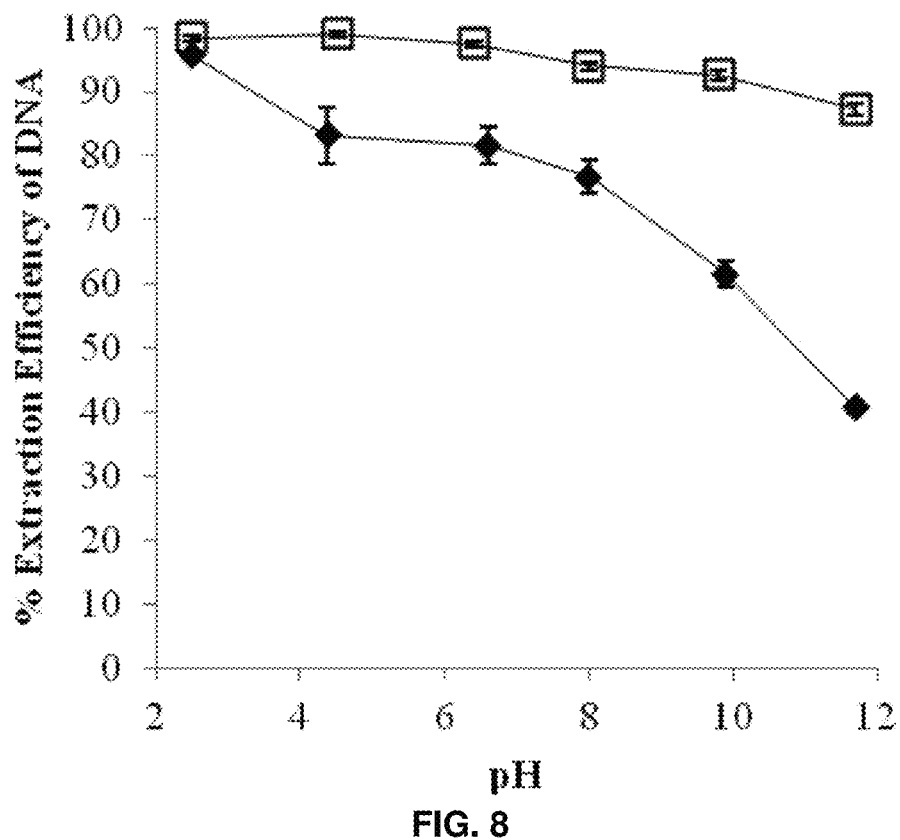
FIG. 8: Effect of aqueous solution pH on the extraction efficiency of stDNA using MIL-based dispersive droplet extraction. Open squares (□) represent the $[P_{6,6,6,14+}][FeCl_4—]$ MIL, while diamonds (♦) indicate the $[(C_{16}BnIM)_2C_{12}^{2+}][NTf2-, FeCl_3Br—]$ MIL.

As shown in FIG. 8, the [P$_{6,6,6,14+}$][FeCl$_4$] MIL exhibited extraction efficiencies greater than 87% across the pH range studied. Furthermore, the extraction efficiency of stDNA for the [P$_{6,6,6,14+}$][FeCl$_4$] MIL showed little dependence on the pH of the solution. In contrast, a considerable decrease in extraction efficiency was observed when the [(C$_{26}$BnIM)$_2$C$_{12}$$^{2+}$][NTf2-, FeCl$_3$Br—] MIL was used to extract stDNA from increasingly basic solutions. In order to maintain high extraction efficiency while avoiding the harsh pH extremes that may compromise the structural integrity of DNA, pH 8 was selected for subsequent extractions.

Extraction of Single-Stranded Oligonucleotides and Duplex DNA

Short length nucleic acids play a central role in molecular recognition and hybridization applications. To determine the usefulness of extracting smaller DNA molecules, MIL-based extraction was applied to short length single-stranded oligonucleotides and duplex DNA. As shown in Table 3, the extraction of low molecular weight dsDNA and ssDNA is MIL-dependent. In the case of the [(C$_8$)$_3$BnN+][FeCl$_3$Br—] MIL, extraction efficiencies of 69.3% and 57.6% were observed for 20 bp DNA and 33-mer ssDNA, respectively. However, the same MIL produced an extraction efficiency of only 41.0% for stDNA indicating that it appears to preferentially extract smaller oligonucleotides. In contrast, the dicationic MIL exhibited higher extraction efficiency values for stDNA than the 20 bp dsDNA, while the [P$_{6,6,6,14+}$][FeCl$_4$—] MIL provided extraction efficiencies exceeding 91% for stDNA, 20 bp dsDNA, and ssDNA. These data show that MILs can be designed that are selective for particular sizes of oligonucleotides or duplex DNA.

TABLE 3

Extraction Efficiencies of dsDNA and ssDNA Using the Three Hydrophobic MILs

| MIL | % extraction efficiency of 20 kbp stDNAa (n = 3) | % extraction efficiency of 20 bp dsDNA[b] (n = 3) | % extraction efficiency of 33-mer ssDNA[c] (n = 3) |
| --- | --- | --- | --- |
| [(C$_{16}$BnIM)$_2$C$_{12}$$^{2+}$][NTf2-, FeCl$_3$Br-] (13) | 76.8 ± 2.6 | 64.0 ± 1.1 | 67.7 ± 3.0 |
| [(C$_8$)$_3$BnN+][FeCl$_3$Br-] (14) | 41.0 ± 0.9 | 69.3 ± 4.4 | 57.6 ± 5.0 |
| [P$_{6,6,6,14+}$][FeCl$_4$-] | 93.8 ± 0.6 | 91.4 ± 0.3 | 94.0 ± 0.2 | aConditions: 4.17 nM; total solution volume: 2 mL; pH 8; volume of MIL 20 μL; manual agitation time: 30 s.
[b]Conditions: 1224 nM; other conditions held constant.
[c]Conditions: 1499 nM; other conditions held constant.

Extraction of DNA from a Complex Matrix

The effect of biologically relevant impurities on MIL-based DNA extraction was examined A complex matrix was simulated through the addition of metal ions or proteins (albumin) to an aqueous solution of DNA.

Figure 9:
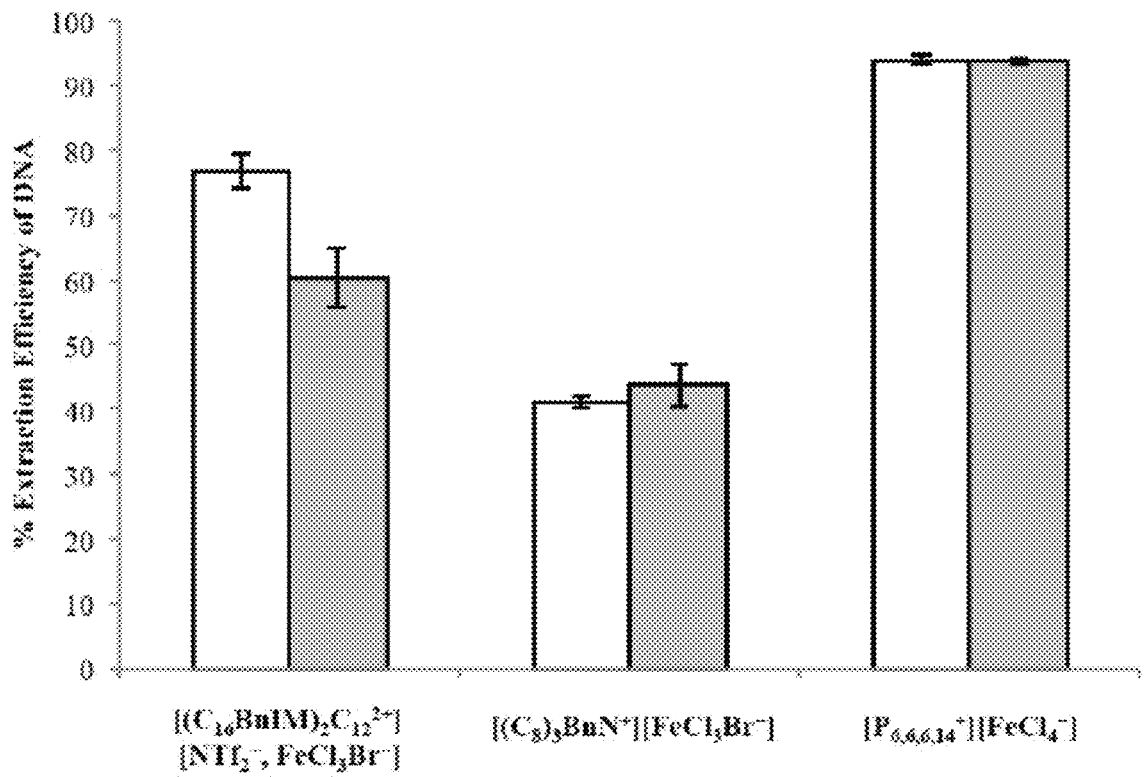
FIG. 9: Comparison of stDNA extraction efficiencies for three hydrophobic MILs from both a neat solution and a matrix containing metal ions (NaCl, KCl, $CaCl_2.2H_2O$, and $MgCl_2.6H_2O$). Open bars represent DNA extraction from a neat aqueous solution, while gray bars indicate extraction of DNA from a matrix containing metal ions.

The extraction performance of the [(C$_{16}$BnIM)$_2$C$_{12}$$^{2+}$][NTf2-, FeCl$_3$Br—], [(C$_8$)$_3$BnN+][FeCl$_3$Br—], and [P$_{6,6,6,14+}$][FeCl$_4$—] MILs was evaluated for 20 kbp stDNA in the presence of NaCl, KCl, CaCl$_2$.2H$_2$O, and MgCl$_2$.6H$_2$O. FIG. 9 shows that the extraction efficiency for the dicationic ([C$_{16}$BnIM)$_2$C$_{12}$$^{2+}$][NTf2-, FeCl$_3$Br—] MIL was somewhat diminished by the addition of the mono- and divalent metal ions, in contrast to what was observed for monocationic imidazolium-based ILs. A very small to negligible variation in extraction efficiencies was observed for the [(C$_8$)$_3$BnN+][FeCl$_3$Br—] and [P$_{6,6,6,14+}$][FeCl$_4$—] MILs.

Figure 10A:
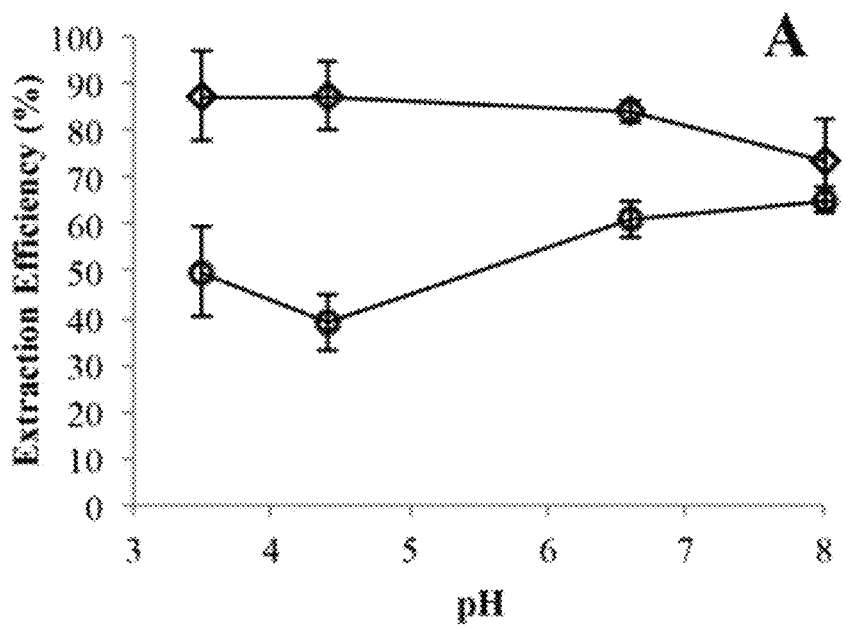
FIGS. 10A-10C: Effect of hydrophobic MIL type, pH, and albumin on the extraction efficiency of 20 kbp stDNA.
Figure 10B:
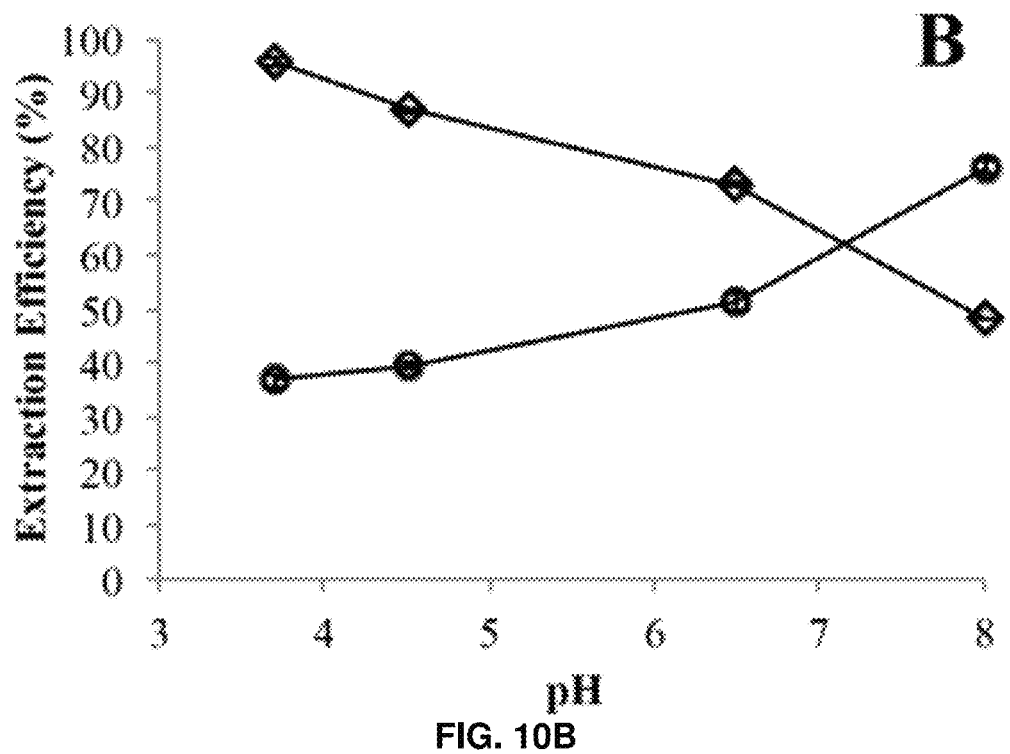
Figure 10C:
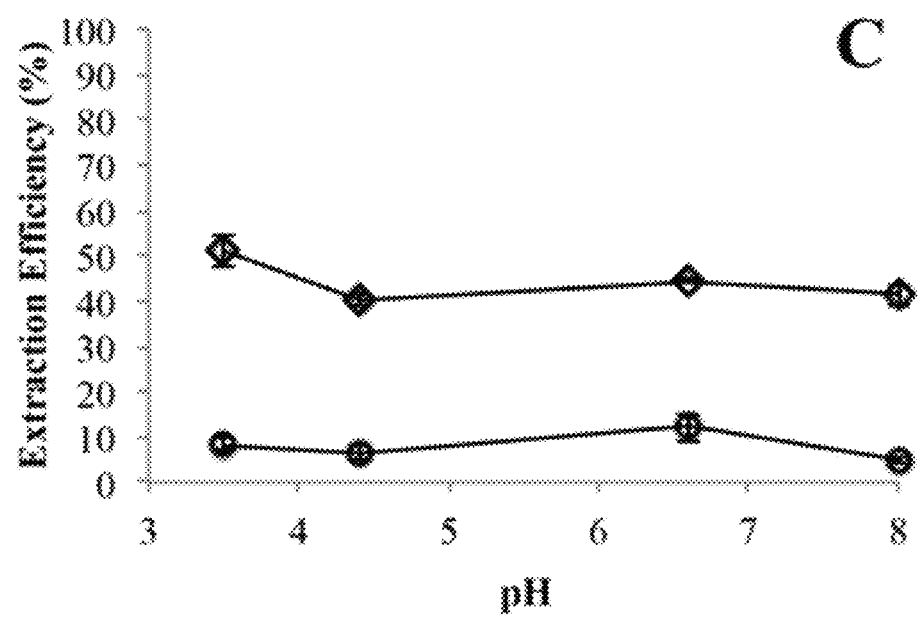

The effect of protein on the extraction efficiency of DNA was done by preparing aqueous 20 kbp stDNA solutions containing albumin as a model protein. The extraction efficiencies of both stDNA and albumin were monitored over a pH range from 3.5 to 8. As shown in FIGS. 10A-10C, each of the three MILs exhibited unique extraction behavior in the presence of stDNA and albumin.

FIG. 10A shows that high extraction efficiencies for both stDNA and albumin were obtained using the dicationic [(C$_{16}$BnIM)$_2$C$_{12}$$^{2+}$][NTf2-, FeCl$_3$Br—] MIL at pH 8. Interestingly, a comparison of FIG. 8 and FIG. 10A reveals that the extraction efficiencies of stDNA in the absence of albumin were similar to those observed after albumin had been spiked into the aqueous solution. However, FIG. 8 and FIG. 10B show that the extraction efficiency of stDNA for the [P$_{6,6,6,14+}$][FeCl$_4$—] MIL was decreased by 46% in the presence of albumin at pH 8. As shown in FIG. 10C, the [(C$_8$)$_3$BnN+][FeCl$_3$Br—] MIL provided relatively lower extraction efficiencies of stDNA across the pH range studied.

With an isoelectric point of 4.6, albumin possesses an overall negative charge at higher pH and may compete with DNA by also engaging in electrostatic interactions with the MIL cation. To examine this effect, the pH of the sample solution was lowered which resulted in a corresponding decrease in the amount of extracted albumin for the [P$_{6,6,6,14+}$][FeCl$_4$—] and [(C$_{16}$BnIM)$_2$C$_{12}$$^{2+}$][NTf2-, FeCl$_3$Br—] MILs. Furthermore, lowering of the sample pH significantly enhanced the extraction efficiency of stDNA for the [P$_{6,6,6,14+}$][FeCl$_4$—] MIL. Although these results show that electrostatic interactions between the MIL and albumin are diminished at low pH, coextraction of albumin was still observed for all three MILs investigated. While not wishing to be bound by theory, it is now believed this may be due to interactions between the hydrophobic amino acid side chains of albumin and the long alkyl groups of the MIL cations that promote the extraction of protein, regardless of solution pH. As shown in FIG. 10C, the coextraction of albumin was less pronounced when employing the [(C$_8$)$_3$BnN+][FeCl$_3$Br—] MIL. Although it extracted less stDNA compared to the other two MILs, the [(C$_8$)$_3$BnN+][FeCl$_3$Br—] MIL exhibited an albumin extraction efficiency of just 5.0% at pH 4.4, while the [(C$_{16}$BnIM)$_2$C$_{12}$$^{2+}$][NTf2-, FeCl$_3$Br—] and [P$_{6,6,6,14+}$][FeCl4-] MILs produced extraction efficiencies nearing 40% at the same pH. These data show that DNA extracted by the [(C$_8$)$_3$BnN+][FeCl$_3$Br—] MIL microdroplet may have less protein contamination than DNA extracted by the other two MILs under the same conditions. The extraction behavior of these MILs shows that MIL-based solvents are capable of enhancing the selectivity toward DNA in the presence of proteins.

Recovery of DNA from the MIL Extraction Phase

Figure 11:
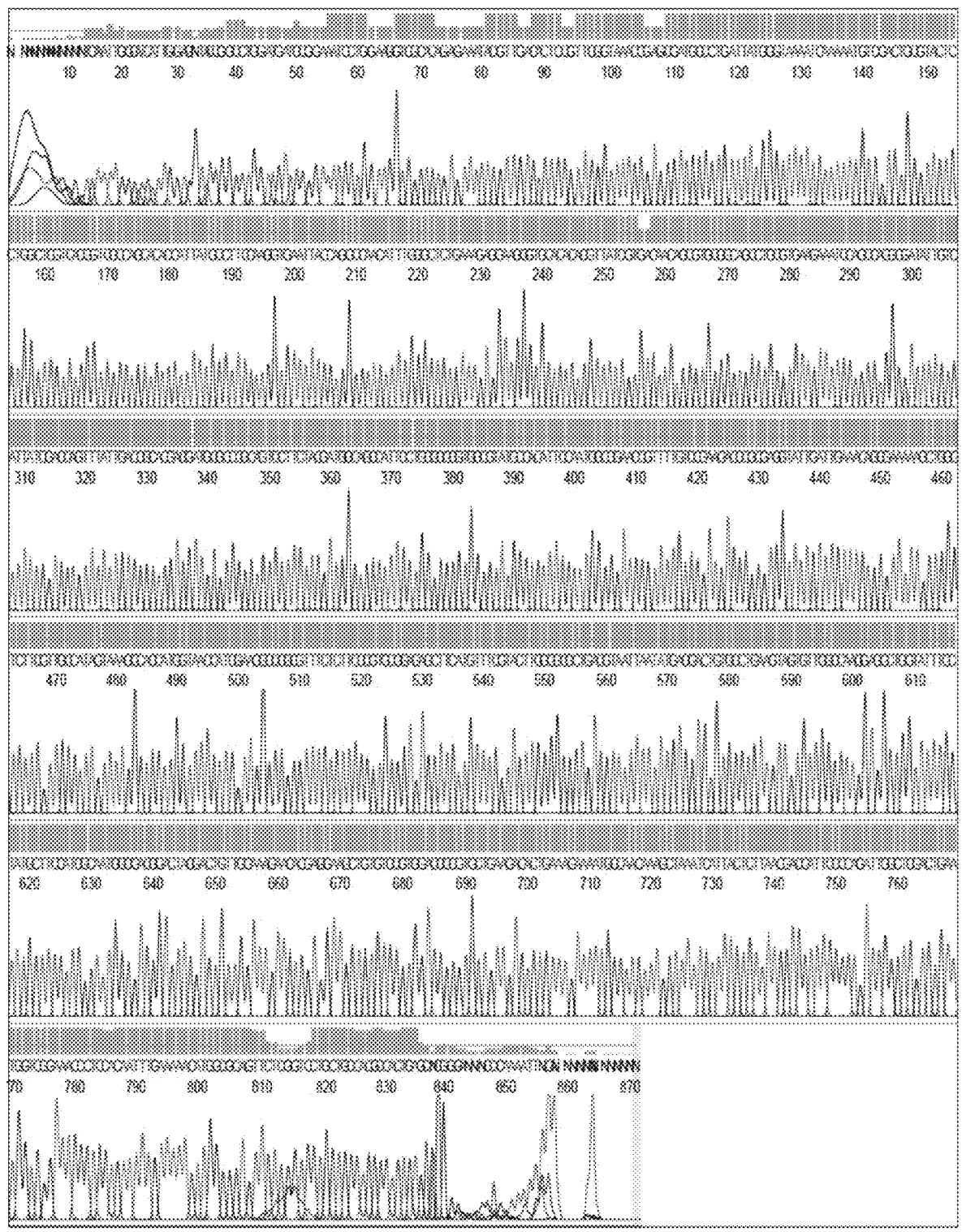
FIG. 11: Electropherogram obtained from the sequencing of the MTAP gene amplified from pDNA extracted by the $[(C^8)_3BnN+][FeCl_3Br—]$ MIL (SEQ ID NO: 5).
Figure 12:
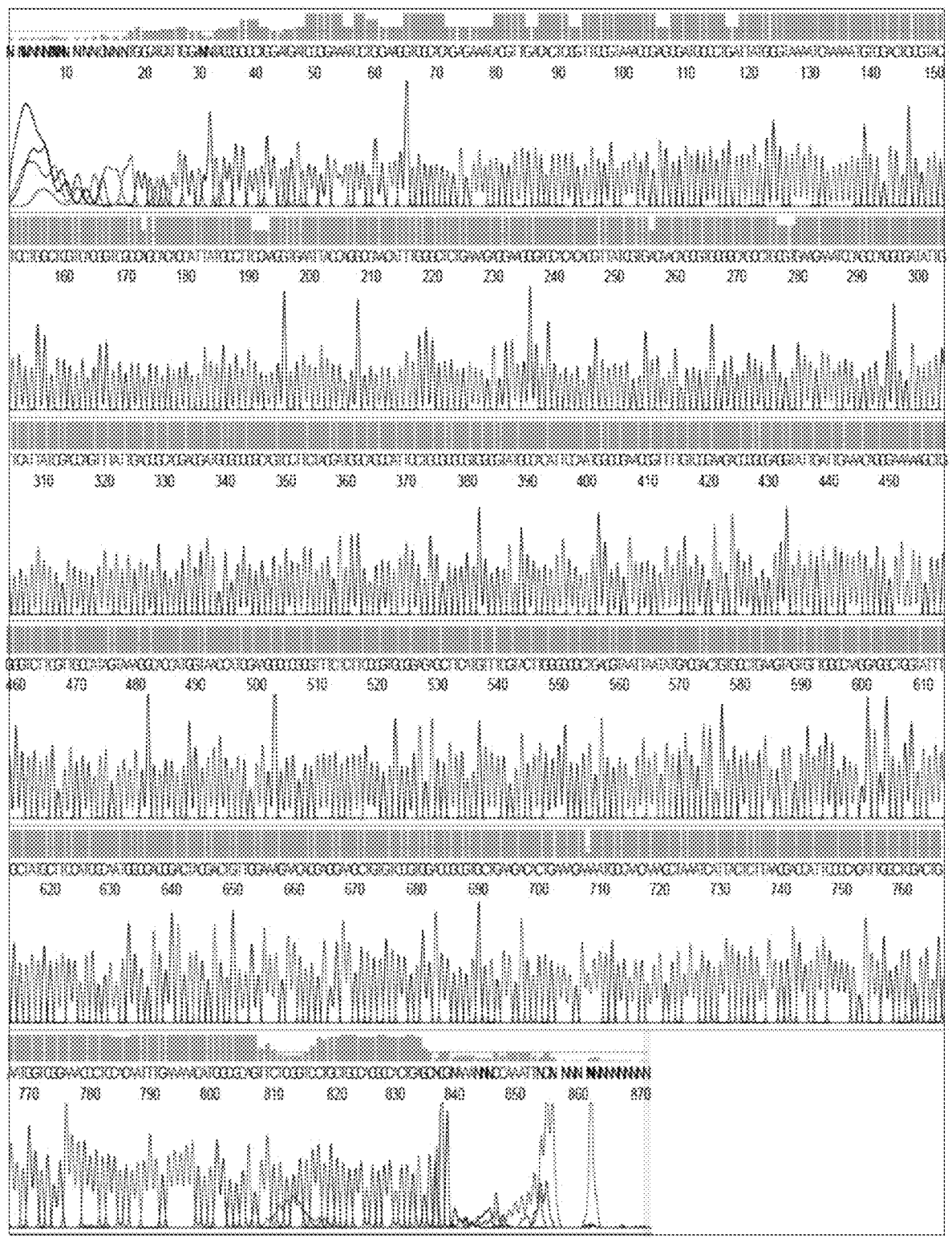
FIG. 12: Electropherogram obtained from the sequencing of the MTAP gene amplified from standard pDNA (SEQ ID NO: 6).

The recovery of high quality DNA following an extraction step is important for accurate downstream analysis, especially in PCR and DNA sequencing experiments. To ensure that DNA extraction performed by the MIL solvent did not alter any portion of the DNA sequence, pDNA extracted by the [(C$_8$)$_3$BnN+][FeCl$_3$Br—] MIL was subjected to sequence analysis. The MTAP gene sequence obtained from pDNA extracted by the MIL and the sequence of a pDNA standard are shown in FIG. 11 and FIG. 12, respectively. The pDNA extracted by the MIL was shown to contain a MTAP gene identical to the standard, indicating that the pDNA was not altered during the MIL extraction step or that the amount of any alterations to the integrity of the biomolecule are sufficiently low to be detected.

To assess the total quantity of DNA recovered after MIL-based DNA extraction, a 4.17 nM solution of stDNA was extracted using the [(C$_8$)$_3$BnN+][FeCl$_3$Br—] MIL. After dissolution of the stDNA-enriched MIL microdroplet in 3 M potassium acetate (pH 4.8), the sample was loaded onto silica sorbent. The sorbent was flushed with 1 mL of isopropanol, and the first fraction was collected, which contained stDNA and excess salt. The stDNA was precipitated with cold ethanol, and the excess salt was removed by washing the pellet with 80% ethanol. In this approach, HPLC analysis determined the recovery of stDNA from the MIL microdroplet to be 57±6%. The yield of the MIL-based DDE method was 23.5 μg of stDNA. Comparatively, a QIAamp DNA Mini Kit was capable of recovering 84±5% of the stDNA from a 4.17 nM solution with a yield of 84.4 μg.

Extraction of DNA from Bacterial Cell Lysate

To show the applicability of the MIL-based DNA extraction method, pDNA in an *E. coli* cell lysate was extracted using the [(C$_8$)$_3$BnN+][FeCl$_3$Br—] MIL and subjected to PCR. This MIL was chosen to minimize protein coextraction. The following two methods were employed for the isolation of DNA from the MIL extraction phase: an approach targeting greater quantities of high purity DNA and a rapid approach for recovering a sufficient quantity of high quality template DNA for PCR. In order to assess whether each recovery procedure was capable of isolating PCR-amplifiable DNA from *E. coli*, pDNA was extracted from a bacterial cell lysate using the [(C$_8$)$_3$BnN+][FeCl$_3$Br—] MIL and subjected to both the silica-based and the rapid immersion method.

Figure 13:
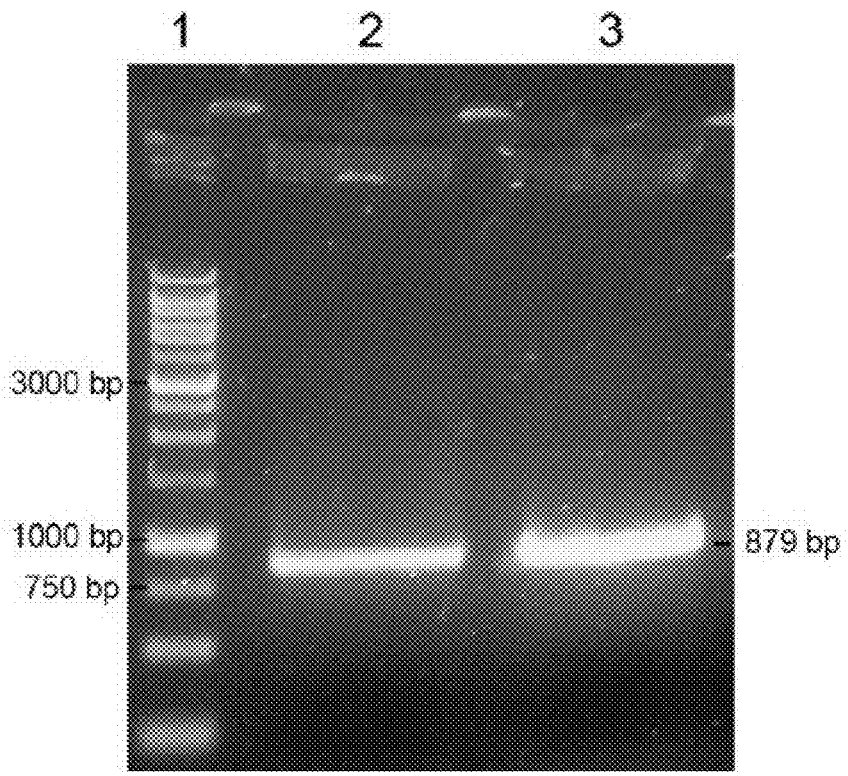
FIG. 13: Agarose gel electrophoresis of the MTAP gene after PCR amplification from pDNA recovered from the $[(C_8)_3BnN+][FeCl_3Br—]$ MIL extraction phase. Lane 1: a 250-25,000 bp DNA ladder. Lane 2: PCR products from pDNA recovered by rapid immersion of the DNA-enriched microdroplet in Tris-HCl. Lane 3: PCR products obtained from pDNA recovered by semi-exhaustive DNA recovery.

As shown in FIG. 13, the silica-based method provided a more intense PCR product band (Lane 3) than did the rapid immersion approach (Lane 2). Nonetheless, immersion of the pDNA-enriched MIL microdroplet in Tris-HCl for just 2 min was capable of transferring sufficient pDNA for PCR amplification and visual detection of the MTAP gene on an agarose gel. This method is especially useful for high throughput nucleic acid analyses, such as the rapid screening of an environmental sample for microorganisms or identification of DNA biomarkers in virtually any sample.

Discussion of Example 2

Hydrophobic MILs were employed as solvents for the extraction of DNA from aqueous solution. The MIL-based method allows for rapid, highly efficient extractions providing a DNA-enriched microdroplet that is easily manipulated in aqueous solution by application of a magnetic field. Higher extraction efficiencies were obtained for shorter oligonucleotides and DNA duplexes with the [(C$_8$)$_3$BnN+] [FeCl$_3$Br—] MIL, while the dicationic [(C$_{16}$BnIM)$_2$C$_{12}$$^{2+}$] [NTf2-, FeCl$_3$Br—] MIL afforded higher extraction efficiencies for the much longer stDNA. MIL-based extraction of stDNA from a complex matrix containing albumin further show the desirable extraction profiles for the MILs, revealing competitive extraction behavior for the [P$_{6,6,6,14+}$] [FeCl$_4$—] MIL and less pronounced coextraction for the [(C$_8$)$_3$BnN+][FeCl$_3$Br—] MIL. These results show how the structural customization of MILs is useful to achieve enhanced selectivity toward a variety of DNA samples. The recovery of DNA from the MIL extraction phase which was determined to be 57±6%, is also shown herein. Furthermore, sequence analysis demonstrated that the DNA recovered from the MIL extraction phase was intact and the sequence unmodified. Plasmid DNA from a bacterial cell lysate was extracted using MIL-based DDE and shown to provide sufficient pDNA quantity and quality for PCR. Further, these MILs are especially useful as solvent systems in many other applications. One non-limiting application is in microfluidic devices where their paramagnetic properties can be exploited for precise control of sample movement.

Example 3

Analysis of Bacterial Plasmid DNA by Solid-Phase Micro Extraction

A cross-linked PIL sorbent coating consisting of a dicationic IL based cross-linker 1,12-bis(3-vinylimidazolium) dodecane dibromide ([VIM)$_2$C$_{12}$$^{2+}$]2[Br$^-$]) and 1-vinyl-3-hexylimidazolium chloride ([VHIM$^+$] [Cl$^-$]) monomer was used for the extraction and preconcentration of plasmid DNA (pDNA) from bacterial cells. The PIL-based SPME method was capable of extracting sufficient template pDNA after 5 min from a 20 ng/mL solution for subsequent PCR amplification and visualization on an agarose gel. Due to favorable electrostatic interactions afforded by the PIL-based sorbent coating, a greater quantity of template pDNA was extracted from aqueous solution compared to a commercial polyacrylate (PA)-based sorbent coating under similar extraction conditions. The PIL sorbent was successfully applied for the extraction of two different plasmids from a mixture of *E. coli* transformants.

Reagents 1-vinylimidazole, 1-chlorohexane, 1,12-dibromododecane, 2-hydroxy-2-methylpropiophenone (DAROCUR 1173), and vinyltrimethoxysilane (VTMS) were purchased from Sigma-Aldrich (Milwaukee, Wis., USA). Methanol, concentrated hydrogen peroxide (30% (w/w)), hydrochloric acid, sodium chloride, tris(hydroxymethyl)aminomethane hydrochloride (Tris-HCl), acetic acid, boric acid, phosphoric acid, and sodium hydroxide were obtained from Fisher Scientific (Fair Lawn, N.J., USA). Deionized water (18.2 MΩ cm) was obtained from a Milli-Q water purification system (Millipore, Bedford, Mass., USA). Elastic nitinol wires with an outer diameter of 125 μm were purchased from Nitinol Devices & Components (Fremont, Calif., USA). A UV reactor equipped with a spinning carousel was obtained from Southern New England Ultraviolet Company (Bradford, Conn., USA). Amber glass vials (10 mL), screw caps with polytetrafluoroethylene septa, and an 85 μm polyacrylate (PA) fiber were obtained from Supelco (Bellefonte, Pa., USA). Polypropylene microcentrifuge tubes were purchased from Fischer Scientific. Modified pET-32 plasmids were obtained from EMD Millipore (Billerica, Mass., USA). NEB 5-alpha Competent *E. coli* cells and Phusion High-Fidelity DNA Polymerase and 5× Phusion HF buffer were obtained from New England Biolabs (Ipswich, Mass., USA). A deoxyribonucleoside triphosphate (dNTP) mix (10 mM each) was obtained from Thermo Scientific (Pittsburgh, Pa., USA). Agarose and tris(hydroxymethyl)aminomethane (Tris) were purchased from P212121 (Ypsilanti, Mich., USA). A 1 Kb Plus DNA Ladder (250-25,000 bp) was obtained from Gold Biotechnology, Inc. (St. Louis Mo., USA). SYBR® Safe DNA gel stain was supplied by Life Technologies (Carlsbad, Calif., USA) and bromophenol blue was purchased from Santa Cruz Biotech (Dallas, Tex., USA).

Preparation of PIL-Based SPME Fiber

Figure 14:
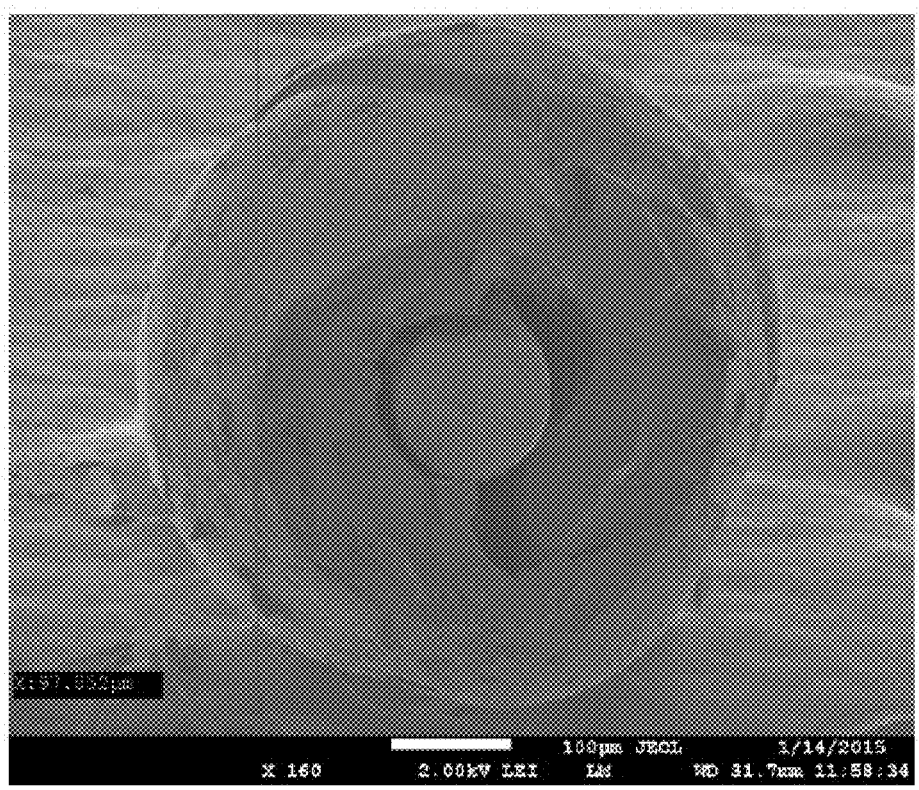
FIG. 14: SEM image showing the cross-section of the PIL sorbent coating used for extracting pDNA from aqueous solution after 40 extractions.

The IL monomer ([VHIM$^+$][Cl$^-$]) and the dicationic IL cross-linker ([(VIM)$_2$C$_{12}$$^{2+}$] 2[Br$^-$]) were synthesized. Cross-linked PIL-based SPME fibers were prepared. Briefly, the nitinol support was immersed in boiling hydrogen peroxide at 70-75° C. for 2 h to generate free hydroxyl groups on the surface of the substrate. The derivatized surface was then reacted with neat VTMS at 85° C. for 2 h. A 1 cm length of the metallic alloy fiber was then dip-coated with a mixture containing the IL monomer, 50% (w/w) cross-linker with respect to monomer, and 3% (w/w) DAROCUR 1173. Afterwards, the fiber was exposed to 254 nm UV light for 2 h. The PIL-based SPME fiber was then immersed in 100 μL of methanol for 15 mM, followed by washing in 10 mL of 20 mM Tris-HCl for 30 mM. A JEOL JSM-7500F scanning electron microscope (SEM) was used to characterize the PIL-based SPME fiber. A SEM image of a PIL-based fiber after 40 extractions is shown in FIG. 14. The average film thickness of the PIL sorbent coating was found to be approximately 65 μm, which is slightly less than the film thickness of the commercial PA fiber (85 μm) examined in this example.

Cell Cultures

Competent *E. coli* cells were transformed with a modified pET-32 plasmid (5.9 kbp) containing either the 879 bp human 5'-methylthioadenosine phosphorylase (MTAP) gene or the 1275 bp vaccinia virus K4 gene. The transformed cells were cultured in 120 mL of Luria Bertani (LB) media with 100 μg/mL carbenicillin at 37° C. for 20 h. Optical density measurements were performed at 600 nm using a Nicolet Evolution 300 UV-vis spectrophotometer from Thermo Scientific. Purified pDNA was obtained from the culture with a QIAprep Spin Miniprep Kit (Qiagen, Valencia, Calif., USA) according to the manufacturer's instructions. The concentration of the pDNA standards were measured using a Synergy H4 Hybrid Microplate Reader from BioTek (Winooski, Vt., USA).

PIL-Based SPME of pDNA

The buffer was prepared using a mixture of 0.04 M of boric acid, phosphoric acid, and acetic acid. The desired pH was obtained by adjusting with sodium hydroxide or hydrochloric acid. Solutions containing either *E. coli* cells or purified pDNA were prepared in 10 mL of the buffer immediately prior to PIL-based SPME. The number of cells added to solution was approximated using OD$_{600}$ values. pDNA was extracted by immersing the SPME fiber in the solution under agitation at 650 rpm. Following extraction, the pDNA was desorbed by placing the PIL fiber in a solution containing 50 μL of 1 M NaCl and 20 mM Tris-HCl for 15 mM. A 2 μL aliquot of the desorption solution was then subjected to PCR amplification. The PIL fiber was washed using 2×10 mL of 1 M NaCl in the buffer for 5 mM before further use.

PCR and Amplicon Visualization

Immediately prior to PCR amplification, 0.03% (w/v) of Brij-700 was added to the desorption solution and incubated at room temperature for 15 mM with gentle mixing to prevent adsorption of the nucleic acid to the polypropylene tube. A 2 μL aliquot of the desorption solution was then transferred to a PCR tube containing 34.5 μL of deionized water and 10 μL of 5× Phusion HF buffer. The MTAP and K4 genes were amplified using the primers 5'-TGC TGT TCC AGG GAC CT-3' [SEQ ID NO:3] and 5'-GAA TTC GGA TCC GGA CGC-3' [SEQ ID NO:4] at a final concentration of 0.2 μM.

Finally, 1 μL from a 10 mM stock solution of dNTPs was added to the reaction mixture along with 1 unit of Phusion High Fidelity DNA Polymerase. Amplification of the MTAP and K4 genes was performed using a Techne FTgene2D thermal cycler (Burlington, N.J., USA). Thermal conditions for the amplification of both genes consisted of 5 mM initial denaturation at 95° C. followed by 30 cycles of denaturation (95° C. for 30 s), annealing (54° C. for 45 s), and elongation (72° C. for 45 s).

PCR products were loaded onto a 1% agarose gel and separated using a BRL H4 Horizontal Gel Electrophoresis System from Life Technologies with a Neo/Sci dual output power supply (Rochester, N.Y., USA). Gels were visualized on a Safe Imager™ 2.0 blue-light transilluminator from Life Technologies. The intensities of the DNA bands were measured using ImageJ software (National Institutes of Health).

Preconcentration of pDNA Using SPME Fibers

Figure 15:
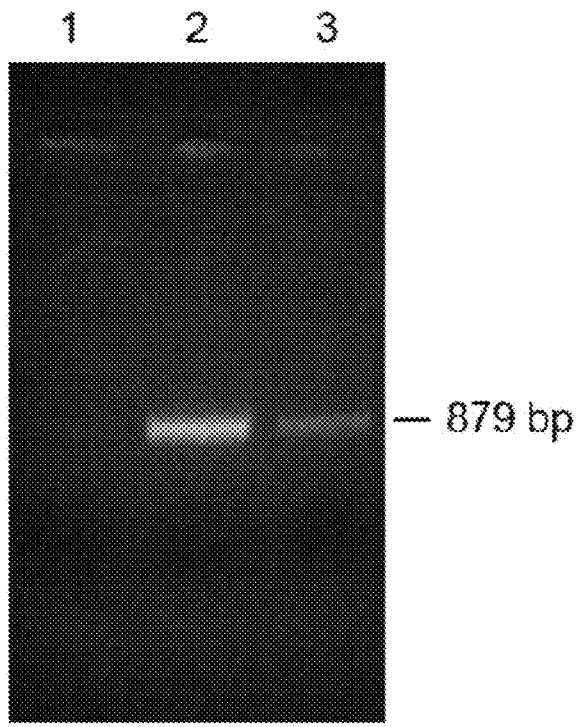
FIG. 15: Amplicon obtained following the preconcentration of 6.7 kbp pDNA from aqueous solution using PIL and commercial PA SPME fibers. Lane 1: PCR product from a 2 μL aliquot of 20 ng/mL of pDNA solution. Lane 2: PCR product following extraction/preconcentration using PIL-based sorbent coating. Lane 3: PCR product following extraction using PA sorbent coating. Extraction conditions: pDNA concentration: 20 ng/mL; total solution volume: 10 mL; desorption solution: 1 M NaCl in 20 mM Tris HCl; desorption solution volume: 50 μL; pH 4.0; extraction time: 30 mM; desorption time: 15 min.

The analysis of extremely small quantities of DNA invariably requires sample purification and preconcentration prior to downstream procedures. Conventional DNA sample preparation methods involve numerous steps that are time consuming and often require manual operation. The development of SPME sorbent coatings for DNA sample preparation is an important advancement that not only facilitates preconcentration, but also constitutes a platform that is amenable to laboratory, clinical, or field sampling.

pDNA containing the MTAP gene (879 bp) was chosen as a model DNA biomolecule to investigate the extraction performance of the cross-linked PIL and commercial PA SPME fibers. FIG. 15 shows the PCR amplification of the MTAP gene from pDNA extracted from aqueous solution using PIL and PA SPME fibers. As shown in Lane 1, the amplicon is not observed after directly loading 2 μL of the 20 ng/mL pDNA solution onto the gel. This is attributed to an insufficient amount of template to detect the amplicon after 30 cycles of PCR amplification.

In contrast, preconcentration of pDNA by the PIL or PA fiber provides sufficient template DNA for detection of the amplicon in Lanes 2 and 3, respectively. The intensity of the PCR product band obtained after PIL extraction was calculated to be 4.2 times greater than the band observed for the PA fiber indicating that a greater quantity of pDNA was extracted by the PIL coating. Previously, it was believed that IL-based substrates are capable of engaging in electrostatic interactions with the negatively charged phosphate backbone of DNA molecules. Unlike the PA sorbent coating, however, it is now shown herein that the cross-linked PIL coating possesses ion-exchange sites that favor electrostatic interactions and lead to superior enrichment of pDNA.

Optimization of Extraction and Desorption Conditions

Figure 16:
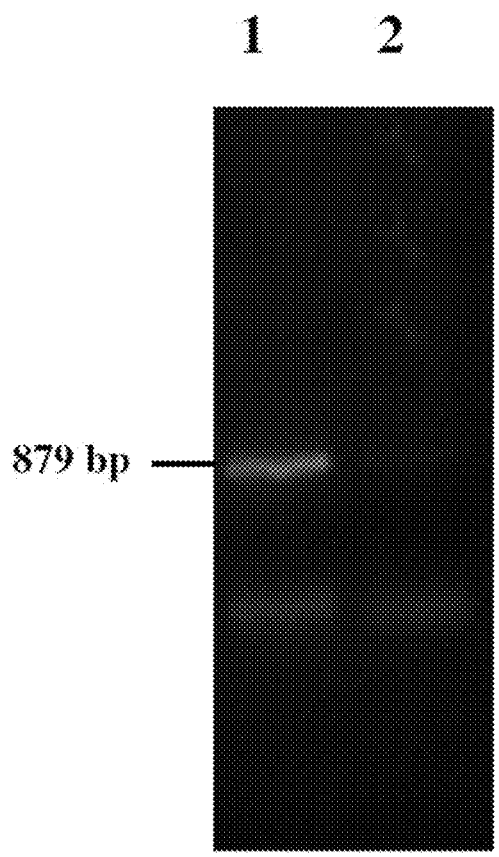
FIG. 16: Effect of NaCl on desorption of 6.7 kbp pDNA containing MTAP gene (879 bp) from PIL-based sorbent coating. Lane 1: PCR products obtained following extraction and desorption of PIL fiber in aqueous solution containing 1 M NaCl and 20 mM Tris HCl. Lane 2: PCR products obtained following extraction and desorption of PIL fiber in 20 mM Tris HCl solution. Extraction conditions: pDNA concentration: 20 ng/mL; total solution volume: 10 mL; pH 4.0; extraction time: 20 mM; desorption time: 15 min. desorption solution volume: 50 μL.

The nature of the desorption solution has a profound influence on the recovery of pDNA from the PIL-based SPME fiber. As shown in FIG. 16, desorption of the PIL fiber in a solution of 20 mM Tris-HCl after extraction from a 20 ng/mL pDNA solution resulted in no observable amplicon. However, the addition of 1 M NaCl to the desorption solution provided a dramatic improvement in the recovery of pDNA from the sorbent coating. At NaCl concentrations greater than 1 M, inhibition of PCR was observed. In an effort to maximize the recovery of pDNA from the PIL coating while maintaining PCR amplification, 1 M NaCl was used as the desorption solution in all subsequent experiments.

To avoid carryover of pDNA, the PIL-based SPME fiber was washed after each extraction using 2×10 mL of 1 M NaCl in buffer for 5 min. The PIL fiber was then desorbed in 50 µL of 1 M NaCl for 15 min and a 2 µL aliquot of the desorption solution was subjected to PCR. After washing the PIL sorbent, no amplicon band was observed.

An aqueous solution containing 20 ng/mL of pDNA was used to determine the effect of extraction time on PIL-based SPME. The extraction time was varied from 5 to 30 min while the desorption time was held constant at 15 min.

Figure 17:
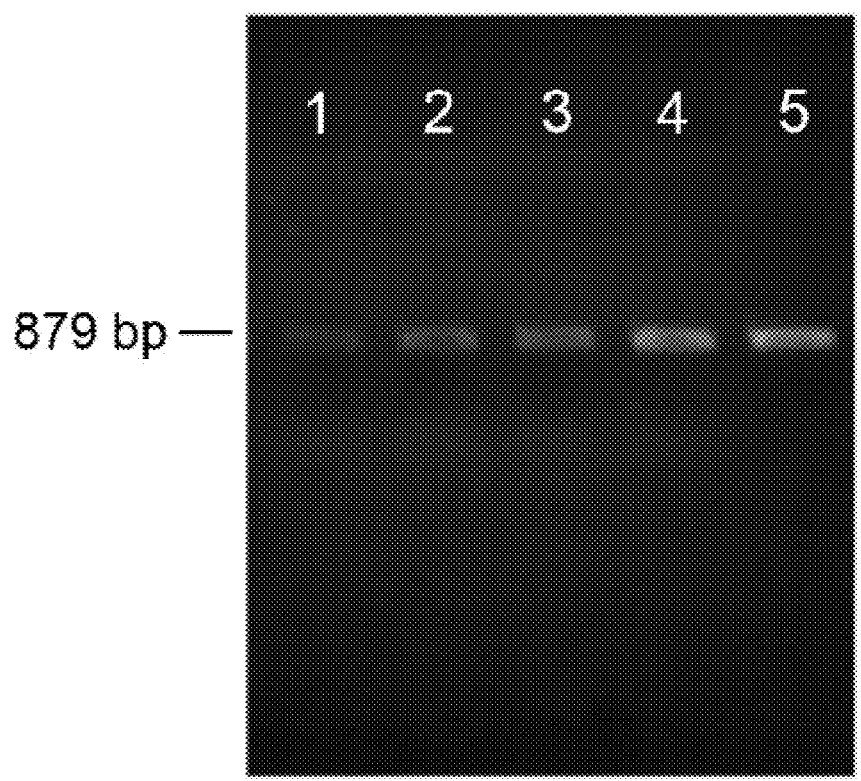
FIG. 17: Effect of extraction time on the extraction of 6.7 kbp pDNA containing the MTAP gene (879 bp). Lane 1: 5 mM; Lane 2: 10 mM; Lane 3: 15 mM; Lane 4: 30 mM. Lane 5: represents a 390 ng MTAP gene standard. Extraction conditions: pDNA concentration: 20 ng/mL; total solution volume: 10 mL; desorption solution: 1 M NaCl in 20 mM Tris HCl; desorption solution volume: 50 μL; pH 4.0; desorption time: 15 mM.

As shown in FIG. 17, an increasing amount of amplicon was obtained as the extraction time was increased. However, beyond an extraction time of 30 min, no significant increase in the amount of pDNA extracted was observed. An extraction time of 20 min was selected as a compromise between extraction time and the amount of pDNA extracted.

Figure 18:
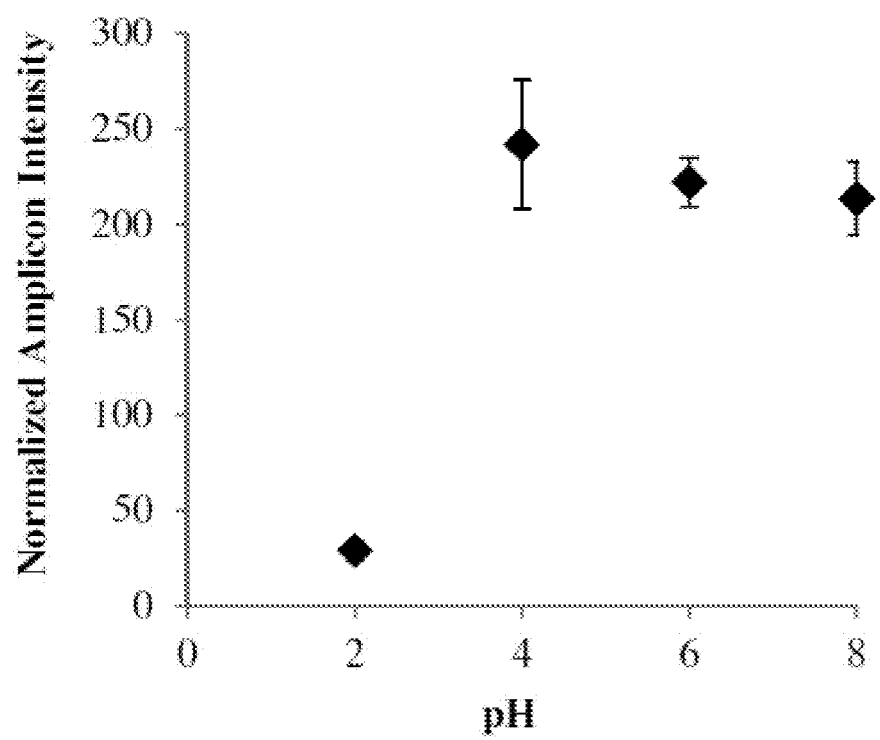
FIG. 18: Effect of aqueous solution pH on the intensity of the amplicon obtained following PIL-based SPME of 6.7 kbp pDNA and PCR amplification of an 879 bp gene. Conditions: pDNA concentration: 20 ng/mL; total solution volume: 10 mL; desorption solution: 1 M NaCl in 20 mM Tris HCl; desorption solution volume: 50 μL; pH 4.0; extraction time: 20 mM; desorption time: 15 mM.

The effect of solution pH on the extraction of pDNA using the PIL-based sorbent coating was studied. Aqueous solutions containing 20 ng/mL of pDNA and pH values ranging from 2 to 8 were examined. As shown in FIG. 18, modest differences in the amount of amplicon were observed from pH 4 to 8 with a slightly higher amount of pDNA being extracted at pH 4.0. In contrast, extraction at pH 2.0 generated the lowest intensity amplicon band, most likely due to degradation of the template pDNA.

Figure 19:
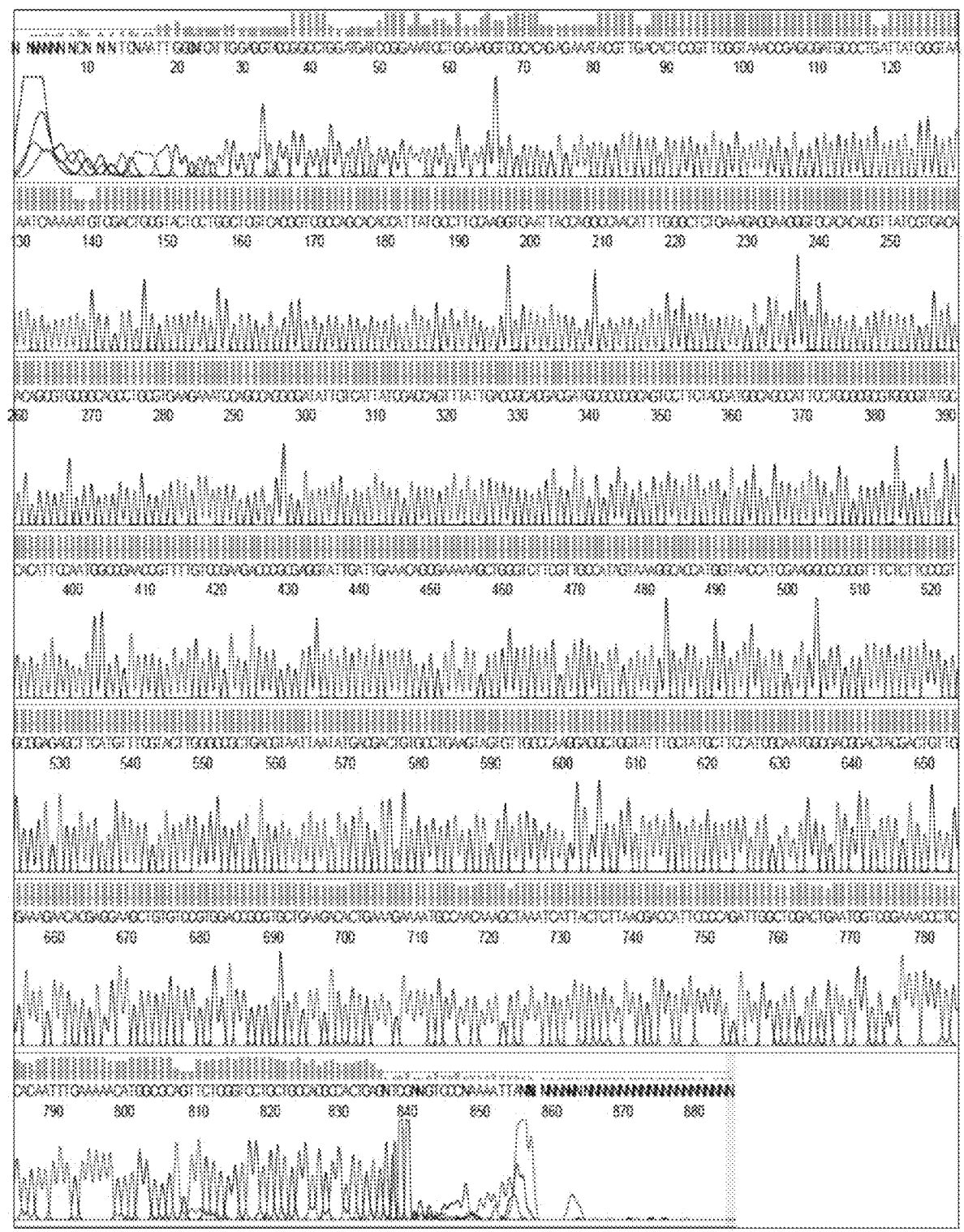
FIG. 19: Electropherogram from the sequencing of the MTAP gene amplified from pDNA extracted by the PIL sorbent coating (SEQ ID NO: 7).
Figure 20:
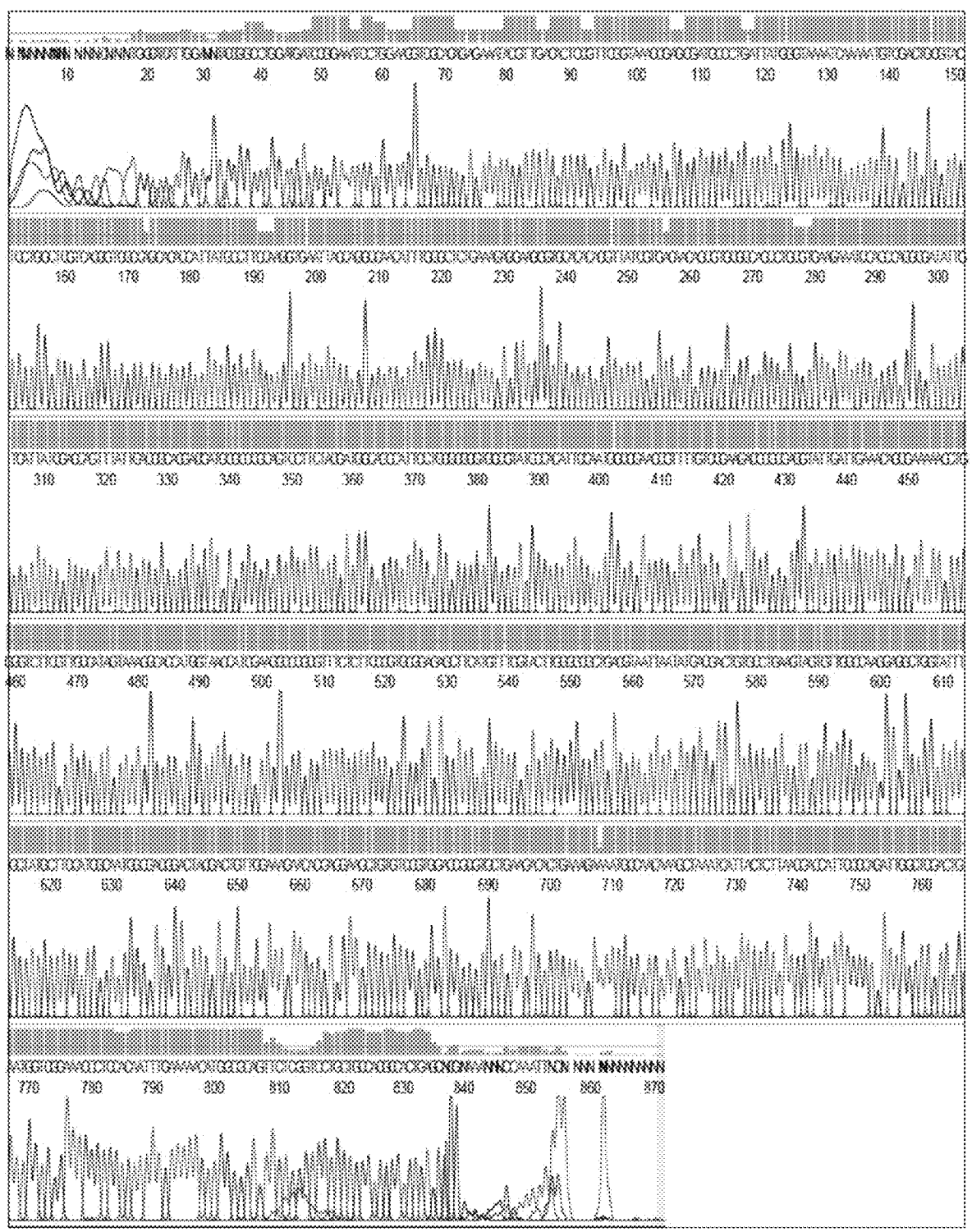
FIG. 20: Electropherogram from the sequencing of the MTAP gene amplified from standard pDNA (SEQ ID NO: 6).

In order to ensure that the sequence of the pDNA remained unaltered following extraction by the PIL coating, the amplified MTAP gene was subjected to sequence analysis. The sequence of the PCR amplified MTAP gene obtained after PIL-based SPME and the sequence of a MTAP gene standard are shown in FIG. 19 and FIG. 20. Comparison of the MTAP gene sequence after PIL-based extraction to the standard revealed no detectable differences, demonstrating the feasibility of PIL-based SPME as a DNA sample preparation technique.

Direct Extraction of pDNA from a Bacterial Cell Culture

Figure 21:
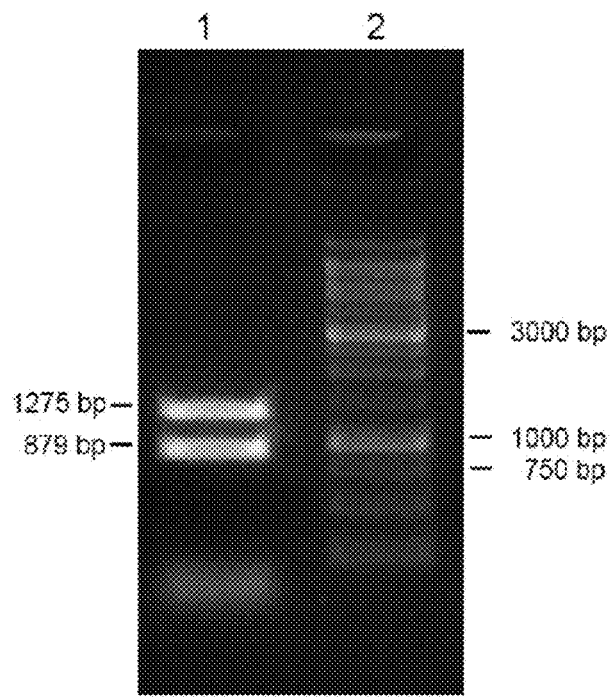
FIG. 21: PCR products obtained following PIL-based SPME of a 1:1 mixture of E. coli cells transformed with pDNA containing either the 1275 bp K4 gene or the 879 bp MTAP gene. Lane 1: PCR products following PIL-based SPME. Lane 2: includes a DNA ladder. Conditions: total solution volume: 10 mL; desorption solution: 1 M NaCl; 20 mM Tris HCl; desorption solution volume: 50 µL; pH 4.0; extraction time: 20 min; desorption time: 15 mM.

The sampling of bacterial DNA from environmental, food, and biological samples is a vital step for the identification of microbial communities and pathogen detection. Frequently, the population of microorganisms in a given sample is diverse. To determine whether the PIL-based SPME method is capable of detecting bacteria from independent cell cultures, E. coli cells transformed with either the MTAP or K4 plasmids were mixed in a 1:1 ratio and diluted to 10 mL with buffer. The total number of cells in solution containing the MTAP plasmid was calculated to be $1.44 \times 10^8$, while $1.35 \times 10^8$ cells contained the K4 plasmid. FIG. 21 shows the PCR products obtained from the desorption solution following PIL-based SPME of the diluted bacterial cells. The bands for the amplified MTAP and K4 genes are of similar intensity, indicating that the length of the gene insert does not affect the relative proportions of pDNA extracted.

Figure 22:
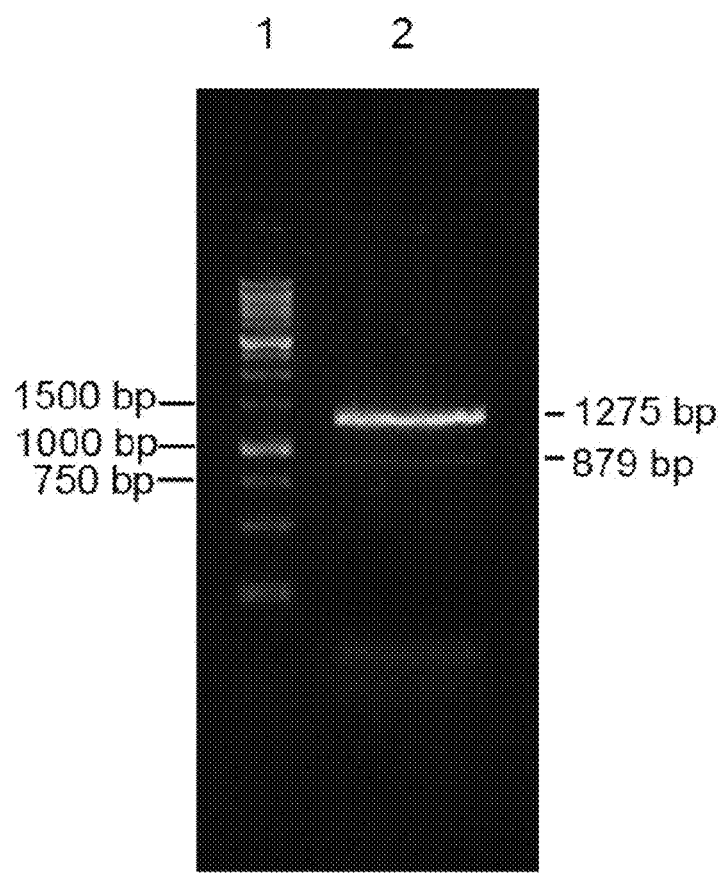
FIG. 22: Detection of pDNA from *E. coli* cells containing either the 1275 bp K4 gene or the 879 bp MTAP gene using the PIL-based SPME method. Lane 1: DNA ladder. Lane 2: PCR products obtained following the extraction of an aqueous solution spiked with $1.36 \times 10^8$ cells containing K4 and $1.44 \times 10^6$ cells containing MTAP. Conditions: total solution volume: 10 mL; desorption solution: 1 M NaCl in 20 mM Tris HCl; desorption solution volume: 50 µL; pH 4.0; extraction time: 20 mM; desorption time: 15 min.

A recurrent cause of bias in the analysis of microbial communities occurs during sampling procedures as a result of disproportionate quantities of unique specimens in the sample. A 10 mL aqueous solution of E. coli transformants possessing either the K4 gene or the MTAP gene (100:1, respectively) was extracted using the PIL sorbent coating. The number of E. coli cells in solution containing the K4 and MTAP genes was $1.36 \times 10^8$ and $1.44 \times 10^6$, respectively. As shown in FIG. 22, bands for both the MTAP and K4 genes were observed following PCR amplification. Normalizing the band intensity for the K4 gene to 1, the MTAP gene produced a band with an intensity of 0.086, reflecting the 100-fold fewer E. coli cells possessing the MTAP gene in solution.

Thus, the PIL-based SPME method is especially useful for the rapid analysis of bacterial contamination in food samples or the determination of microbial diversity in environmental samples. Moreover, the SPME platform is well suited for applications requiring field sampling, further expanding the applicability of the method.

Discussion of Example 3

PIL-based sorbent coatings were used in SPME for the isolation and preconcentration of pDNA from bacterial cells. The PIL sorbent phase exhibited superior extraction of pDNA from aqueous solution compared to a commercial PA sorbent coating. The optimized SPME technique was capable of preconcentrating sufficient pDNA within 5 min for PCR amplification and detection on an agarose gel. Sequence analysis of a target gene from the extracted pDNA confirmed that the integrity of the pDNA sequence was preserved after PIL-based SPME. The developed method was successfully employed for the analysis of two different E. coli transformants from a dilute solution.

While the materials and methods have been described with reference to various and preferred embodiments, it should be understood by those skilled in the art that various changes can be made and equivalents can be substituted for elements thereof without departing from the essential scope of the invention. In addition, many modifications can be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated by reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A magnetic ionic liquid, comprising at least one cationic component and at least one anionic component, wherein at least one of the cationic components or at least one of the anionic components is a paramagnetic component, the magnetic ionic liquid being capable of manipulation by an external magnetic field;

wherein the magnetic ionic liquid comprises a monocationic compound selected from:

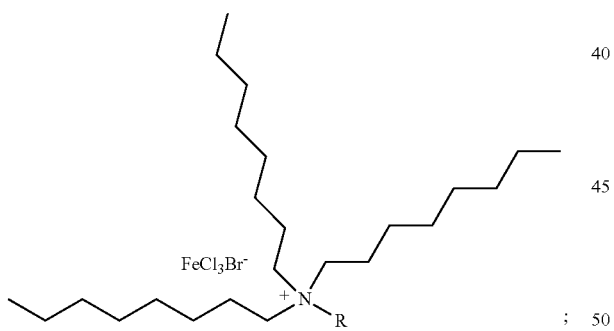

and, wherein R is selected from the group consisting of:

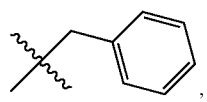 (1)

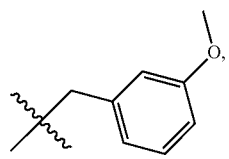 (2)

and

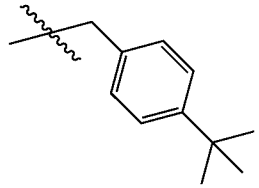 (3)

* * * * *